United States Patent
Feiler et al.

(10) Patent No.: US 11,512,048 B2
(45) Date of Patent: Nov. 29, 2022

(54) HEAT SENSITIVE RECORDING MATERIAL, AND COLOR DEVELOPER

(71) Applicant: Solenis Technologies, L.P., Wilmington, DE (US)

(72) Inventors: Leonhard Feiler, Basel (CH); Frank Bachmann, Basel (CH); Prachin Kolambkar, Mumbai (IN); Vilas Wakhare, Mumbai (IN); Priti Kulkarni, Navi Mumbai (IN); Robert Montgomery O'Neil, Manchester (GB)

(73) Assignee: Solenis Technologies, L.P., Wilmington, DE (US)

( * ) Notice: Subject to any disclaimer, the term of this patent is extended or adjusted under 35 U.S.C. 154(b) by 0 days.

(21) Appl. No.: 16/976,478

(22) PCT Filed: Mar. 1, 2019

(86) PCT No.: PCT/EP2019/055099
§ 371 (c)(1),
(2) Date: Aug. 28, 2020

(87) PCT Pub. No.: WO2019/166608
PCT Pub. Date: Sep. 6, 2019

(65) Prior Publication Data
US 2021/0002215 A1    Jan. 7, 2021

(30) Foreign Application Priority Data
Mar. 2, 2018    (EP) ..................... 18159670

(51) Int. Cl.
*C07C 311/16*    (2006.01)
*B41M 5/333*    (2006.01)
*C07C 303/22*    (2006.01)
*C07C 303/38*    (2006.01)
(Continued)

(52) U.S. Cl.
CPC ......... *C07C 311/16* (2013.01); *B41M 5/3333* (2013.01); *C07C 303/22* (2013.01); *C07C 303/38* (2013.01); *C07C 311/21* (2013.01); *B41M 5/3275* (2013.01)

(58) Field of Classification Search
None
See application file for complete search history.

(56) References Cited

U.S. PATENT DOCUMENTS

2005/0282793 A1*   12/2005   Wyrwa ..................... C07J 1/00
                                                                 514/182
2021/0060994 A1*   3/2021   Kocak ................. B41M 5/3333

FOREIGN PATENT DOCUMENTS

| EP | 0230961 A2 | 1/1987 |
| EP | 0526072 A1 | 2/1993 |
| EP | 0573048 A2 | 12/1993 |

(Continued)

OTHER PUBLICATIONS

ISA/EP, International Search Report and Written Opinion issued in Int. Appl. No. PCT/EP2019/055099 dated Jun. 12, 2019.

(Continued)

*Primary Examiner* — Amy C Bonaparte
(74) *Attorney, Agent, or Firm* — Lorenz & Kopf, LLP

(57) ABSTRACT

The presently claimed invention relates to a color developer, a process for its manufacture and its use as a component in heat sensitive recording material. The heat sensitive recording material is useful for thermographic printing.

19 Claims, 2 Drawing Sheets

(51) Int. Cl.
*C07C 311/21* (2006.01)
*B41M 5/327* (2006.01)

(56) References Cited

FOREIGN PATENT DOCUMENTS

| EP | 1132770 | A2 | | 9/2001 |
|---|---|---|---|---|
| EP | 2923851 | A1 | | 9/2015 |
| FR | 2649698 | A2 | | 9/2015 |
| JP | H07209838 | | * | 8/1995 |
| RU | 2245873 | C2 | | 2/2005 |
| SU | 1691386 | A1 | | 11/1991 |
| WO | 0035679 | A1 | | 6/2000 |
| WO | 2005113575 | A1 | | 12/2005 |

OTHER PUBLICATIONS

Concise Chemical Encyclopedia, "Sovetskaya entsiklopediya" publishing house, Moscow, 1967, vol. 5, cols. 657-661.

* cited by examiner

HEAT SENSITIVE RECORDING MATERIAL, AND COLOR DEVELOPER

CROSS-REFERENCE TO RELATED APPLICATIONS

This application is a U.S. National-Stage entry under 35 U.S.C. § 371 based on International Application No. PCT/EP2019/055099, filed Mar. 1, 2019, which was published under PCT Article 21(2) and which claims priority to European Application No. 18159670.1, filed Mar. 2, 2018, which are all hereby incorporated in their entirety by reference.

Description

The presently claimed invention relates to a color developer, a process for its manufacture and its use as a component in heat sensitive recording material. The heat sensitive recording material is useful for thermographic printing.

Thermographic printing, for example printing point of sales (PoS) receipts, uses so called thermal paper which contains heat sensitive recording material. It is composed of two main components, a color former and a color developer. The color developer forms a colored image after complexation with the color former, which occurs upon heating.

Bisphenol A is a widely used color developer. It is inexpensive and technically sufficient, but under current European chemical legislation it is classified as "toxic for reproduction" and it is suspected that is causes endocrine disruption activity in both humans and in the environment. Therefore, bisphenol A will be restricted in thermal papers placed on the European market from January 2020. Another phenolic color developer, bisphenol S is also under investigation.

The non-phenolic color developers such as, sulfonyl urea derivatives, described in example in EP 526072 or in particular in WO00/35679 such as N-p-toluenesulfonyl-N'-3-(p-toluenesulfonyloxy)phenylurea, or urea derivatives such as described in EP 2923851, offer an alternative to the widely used phenolic products. However, their synthesis requires the use of specialty and semi-specialty raw materials. Consequently, they are costly for widespread use, especially for applications such as point of sales (PoS) and/or economy grades of thermal paper.

Accordingly, it is an object of the present invention to provide a non-phenolic color developer for use in heat sensitive recording materials. Further, it is desired that the color developer is a technically suitable and cost-effective alternative to the hitherto used phenolic and non-phenolic color developers.

SUMMARY OF THE INVENTION

Surprisingly, it is found that compound of formula (I) is appropriate for use in heat sensitive recording materials. The compound of formula (I) is a non-phenolic, technically suitable and cost-effective alternative to the hitherto used phenolic and non-phenolic color developers.

Accordingly, the main aspect of the presently claimed invention is compound of formula (I)

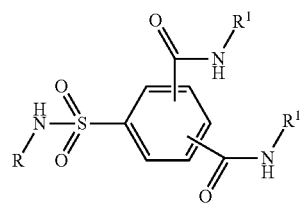

wherein

R and $R^1$ are independently selected from the group consisting of hydrogen, linear or branched $C_1$-$C_{18}$-alkyl, $R^{11}O$—$R^{12}$— wherein $R^{11}$ and $R^{12}$ are independently linear or branched $C_1$-$C_8$-alkyl, $(R^{13})_2N$—$R^{12}$— wherein $R^{13}$ is a linear or branched $C_1$-$C_8$-alkyl or together with the nitrogen to which they are attached form a 5 or 6 membered ring, and $R^{12}$ is as defined earlier, and a radical of formula (II)

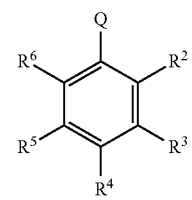

wherein, $R^2$, $R^3$, $R^4$, $R^5$, and $R^6$ are independently selected from the group consisting of hydrogen, linear or branched $C_1$-$C_8$-alkyl, —NH—C(=O)—$R^{14}$, —C(=O)—NH—$R^{14}$, wherein $R^{14}$ is linear or branched $C_1$-$C_8$-alkyl, —C(=O)O$R^{15}$, wherein $R^{15}$ is linear or branched $C_1$-$C_8$-alkyl, and halogen, or $R^2$ and $R^3$, or $R^4$ and $R^5$ or both, or $R^3$ and $R^4$, or $R^5$ and $R^6$ or both, or $R^2$ and $R^3$ as well as $R^5$ and $R^6$ together form a hydrocarbon diradical comprising 3 or 4 carbon atoms;

and

Q is a single bond or branched or unbranched $C_1$-$C_8$-alkylene, optionally comprising one or more oxygen atoms.

In another aspect, the presently claimed invention is directed to the use of the compound of formula (I) as a color developer in a heat sensitive recording material.

In yet another aspect, the presently claimed invention is directed to a heat sensitive recording material comprising A) at least one color former, and
B) at least one color developer of formula (I)

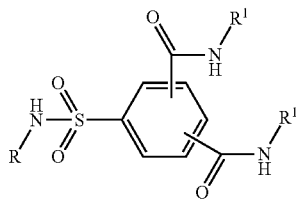

wherein R and R¹ are as defined earlier.

BRIEF DESCRIPTION OF THE DRAWINGS

The disclosure described herein is illustrated by way of example and not by way of limitation in the accompanying figures. For simplicity and clarity of illustration, features illustrated in the figures are not necessarily drawn to scale. For example, the dimensions of some features may be exaggerated relative to other features for clarity.

DETAILED DESCRIPTION

Figure 1:
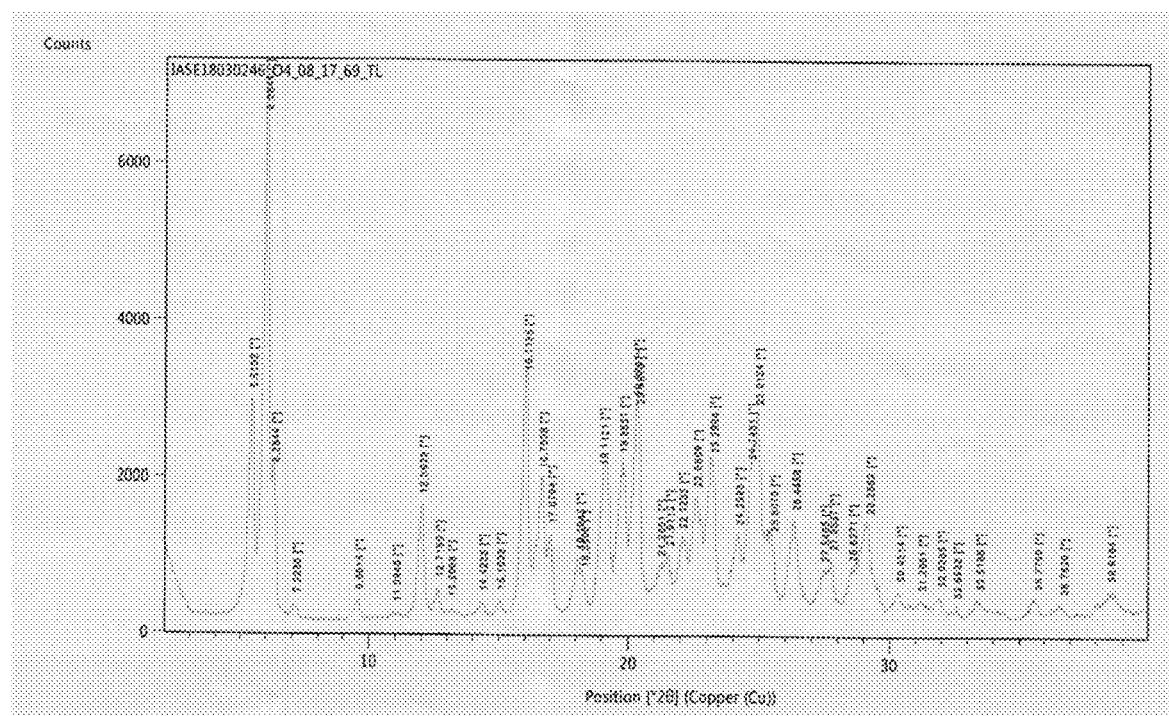
FIG. 1 is X-ray powder diffraction pattern spectrum of the crystalline polymorph form α of compound of formula (III) represented in the form of Bragg angles (2θ/CuK$_α$).
Figure 2:
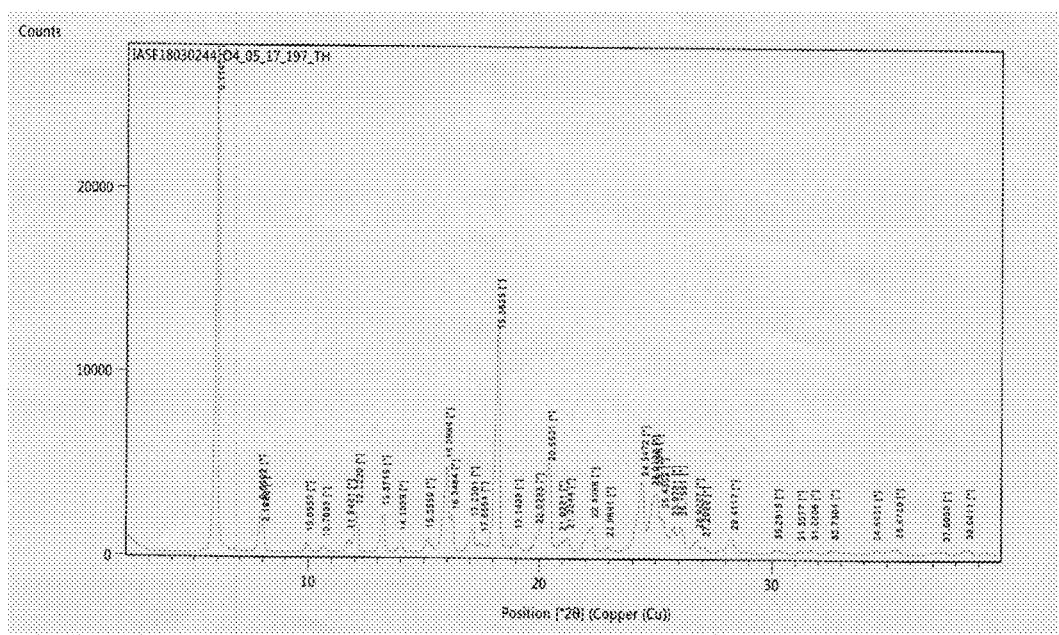
FIG. 2 is X-ray powder diffraction pattern spectrum of the crystalline polymorph form β of compound of formula (III) represented in the form of Bragg angles (2θ/CuK$_α$).

Before the present compositions and formulations of the presently claimed invention are described, it is to be understood that this invention is not limited to particular compositions and formulations described, since such compositions and formulation may, of course, vary. It is also to be understood that the terminology used herein is not intended to be limiting, since the scope of the presently claimed invention will be limited only by the appended claims.

If hereinafter a group is defined to comprise at least a certain number of embodiments, this is meant to also encompass a group which preferably consists of these embodiments only. Furthermore, the terms 'first', 'second', 'third' or a , b , c , etc. and the like in the description and in the claims, are used for distinguishing between similar elements and not necessarily for describing a sequential or chronological order. It is to be understood that the terms so used are interchangeable under appropriate circumstances and that the embodiments of the presently claimed invention described herein are capable of operation in other sequences than described or illustrated herein. In case the terms 'first', 'second', 'third' or '(A)', '(B)' and '(C)' or '(a)', '(b)', '(c)', '(d)', 'ii' etc. relate to steps of a method or use or assay there is no time or time interval coherence between the steps, that is, the steps may be carried out simultaneously or there may be time intervals of seconds, minutes, hours, days, weeks, months or even years between such steps, unless otherwise indicated in the application as set forth herein above or below.

Furthermore, the ranges defined throughout the specification include the end values as well i.e. a range of 1 to 10 implies that both 1 and 10 are included in the range. For the avoidance of doubt, applicant shall be entitled to any equivalents according to applicable law.

In the following passages, different aspects of the presently claimed invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to 'one embodiment' or 'an embodiment' means that a particular feature, structure or characteristic described in connection with the embodiment is included in at least one embodiment of the presently claimed invention. Thus, appearances of the phrases 'in one embodiment' or 'in an embodiment' in various places throughout this specification are not necessarily all referring to the same embodiment, but may.

Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the presently claimed invention, and form different embodiments, as would be understood by those in the art. For example, in the appended claims, any of the claimed embodiments can be used in any combination.

Surprisingly, it has been found that the heat sensitive recording material comprising compound of formula (I) as a color developer has high optical density, humidity resistance, oil resistance and light resistance. The compound of formula (I) is a non-phenolic, technically suitable and a cost-effective color developer. As a result, the compound of formula (I) is a suitable alternative to the hitherto known phenolic and non-phenolic color developers.

Hence, in first aspect, the presently claimed invention is directed to a compound of formula (I)

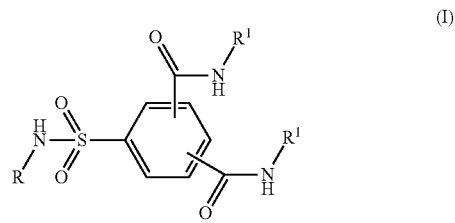

wherein
R and R¹ are independently selected from the group consisting of
  hydrogen,
  linear or branched $C_1$-$C_{18}$-alkyl,
  $R^{11}O$—$R^{12}$— wherein $R^{11}$ and $R^{12}$ are independently linear or branched $C_1$-$C_8$-alkyl,
  $(R^{13})_2N$—$R^{12}$— wherein $R^{13}$ is a linear or branched $C_1$-$C_8$-alkyl or together with the nitrogen to which they are attached form a 5 or 6 membered ring and $R^{12}$ is as defined earlier; and a radical of formula (II)

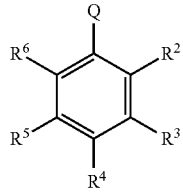

wherein, $R^2$, $R^3$, $R^4$, $R^5$, and $R^6$ are independently selected from the group consisting of hydrogen, linear or branched $C_1$-$C_8$-alkyl, —NH—C(=O)—$R^{14}$, —C(=O)—NH—$R^{14}$, wherein $R^{14}$ is linear or branched $C_1$-$C_8$-alkyl, —C(=O)O$R^{15}$, wherein $R^{15}$ is linear or branched $C_1$-$C_8$-alkyl, and halogen, or $R^2$ and $R^3$, or $R^4$ and $R^5$ or both, or $R^3$ and $R^4$, or $R^5$ and $R^6$ or both, or $R^2$ and $R^3$ as well as $R^5$ and $R^6$ together form a ring comprising 3 or 4 carbon atoms;

and

Q is a single bond or branched or unbranched $C_1$-$C_8$-alkylene, optionally comprising one or more oxygen atoms.

In a more preferred embodiment, the compound of formula (I) is,

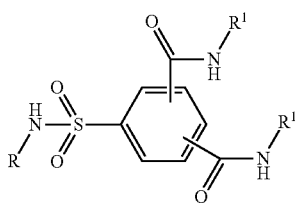

wherein

R and $R^1$ are independently selected from the group consisting of hydrogen, linear or branched $C_1$-$C_{18}$-alkyl, and a radical of formula (II)

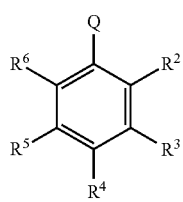

wherein, $R^2$, $R^3$, $R^4$, $R^5$, and $R^6$ are independently selected from the group consisting of hydrogen, linear or branched $C_1$-$C_8$-alkyl, and Q is a single bond.

In a even more preferred embodiment, the compound of formula (I) is

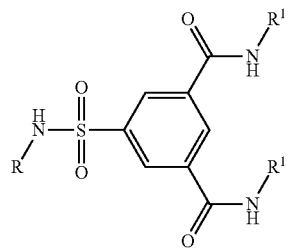

wherein

R and $R^1$ are independently selected from the group consisting of hydrogen, linear or branched $C_1$-$C_{18}$-alkyl, $R^{11}$O—$R^{12}$— wherein $R^{11}$ and $R^{12}$ are independently linear or branched $C_1$-$C_8$-alkyl, $(R^{13})_2$N—$R^{12}$— wherein $R^{13}$ is a linear or branched $C_1$-$C_8$-alkyl or together with the nitrogen to which they are attached form a 5 or 6 membered ring and $R^{12}$ is as defined earlier; and a radical of formula (II)

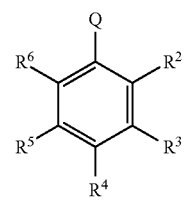

wherein, wherein, $R^2$, $R^3$, $R^4$, $R^5$, and $R^6$ are independently selected from the group consisting of hydrogen, linear or branched $C_1$-$C_8$-alkyl, —NH—C(=O)—$R^{14}$, —C(=O)—NH—$R^{14}$, wherein $R^{14}$ is linear or branched $C_1$-$C_8$-alkyl, —C(=O)O$R^{15}$, wherein $R^{15}$ is linear or branched $C_1$-$C_8$-alkyl, and halogen, or $R^2$ and $R^3$, or $R^4$ and $R^5$ or both, or $R^3$ and $R^4$, or $R^5$ and $R^6$ or both, or $R^2$ and $R^3$ as well as $R^5$ and $R^6$ together form a ring comprising 3 or 4 carbon atoms;

and

Q is a single bond or branched or unbranched $C_1$-$C_8$-alkylene, optionally comprising one or more oxygen atoms.

In a most preferred embodiment, the compound of formula (I) is,

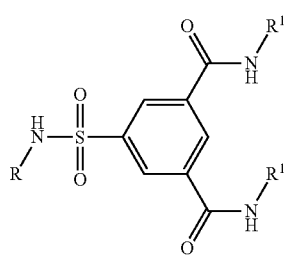

(I)

wherein
R and R¹ are independently selected from the group consisting of hydrogen, linear or branched $C_1$-$C_{18}$-alkyl, and a radical of formula (II)

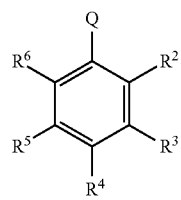

(II)

wherein,
wherein, $R^2$, $R^3$, $R^4$, $R^5$, and $R^6$ are independently selected from the group consisting of hydrogen, linear or branched $C_1$-$C_8$-alkyl, and Q is a single bond.

In a even more preferred embodiment, the compound of formula (I) is selected from the group consisting of 5-(N-benzyl-sulfonylamido)-(N',N"-dibenzyl)-isophthalic acid-diamide, 5-(N-3-methylphenyl-sulfonylamido)-(N',N"-bis-(3-methylphenyl)-isophthalic acid-diamide, 5-(N-2,6-diethylphenyl-sulfonylamido)-(N',N"-bis-(2,6-diethylphenyl)-isophthalic acid-diamide, 5-(N-phenyl-sulfonylamido)-(N',N"-bisphenyl)-isophthalic acid-diamide, 5-(N-o-isopropyl-phenyl-sulfonylamido)-(N',N"-bis-(o-isopropylphenyl)-isophthalic acid-diamide, 5-(N-p-acetamido-phenyl-sulfonylamido)-(N',N"-bis-(p-acetamido-phenyl)-isophthalic acid-diamide, 5-(N-1-tetralino-sulfonylamido)-(N',N"-bis-(1-tetralino)-isophthalic acid-diamide, 5-(N-3-methylphenyl-sulfonylamido)-(N', N"-bis-(3-methylphenyl)-isophthalic acid-diamide, 5-(N-1-phenylethyl-sulfonylamido)-(N',N"-bis-(1-phenylethyl)-isophthalic acid-diamide, 5-(N-2-phenylethyl-sulfonylamido)-(N',N"-bis-(2-phenylethyl)-isophthalic acid-diamide, 5-(N-2,6-diethylphenyl-sulfonylamido)-(N', N"-bis-(2,6-diethylphenyl)-isophthalic acid-diamide, 5-(N-n-butyl-sulfonylamido)-(N',N"-di-n-butyl-isophthalic acid-diamide, 5-(N-2-ethylhexyl-sulfonylamido)-(N',N"-di-2-ethylhexyl-isophthalic acid-diamide, 5-(N-benzyl-sulfonylamido)-(N',N"-diphenyl)-isophthalic acid-diamide, 5-(N-phenyl-sulfonylamido)-(N',N"-dibenzyl)-isophthalic acid-diamide, 5-(N-benzyl-sulfonylamido)-(N',N"-bis-(3-methyl-phenyl)-isophthalic acid-diamide, 5-(N-butyl-sulfonylamido)-(N',N"-bis-(3-methyl-phenyl)-isophthalic acid-diamide, 5-(N-1-phenyl-ethyl-sulfonylamido)-(N',N"-bis-(3-methyl-phenyl)-isophthalic acid-diamide, 5-(N-2-phenyl-ethyl-sulfonylamido)-(N',N"-bis-(3-methyl-phenyl)-isophthalic acid-diamide, 5-(N-2-methoxy-ethyl-sulfonylamido)-(N',N"-bis-(3-methyl-phenyl)-isophthalic acid-diamide, 5-(N-n-octyl-sulfonylamido)-(N',N"-bis-(3-methyl-phenyl)isophthalic acid-diamide, 5-(N-benzyl-sulfonylamido)-(N',N"-bis-(2,6-diethyl-phenyl)-isophthalic acid-diamide, 5-(N-n-octyl-sulfonylamido)-(N',N"-bis-(2,6-diethyl-phenyl)-isophthalic acid-diamide and 5-(N-2-phenoxy-ethyl-sulfonylamido)-(N',N"-bis-(2,6-diethyl-phenyl)-isophthalic acid-diamide.

In a particularly preferred embodiment, the compound of formula (I) is compound (III).

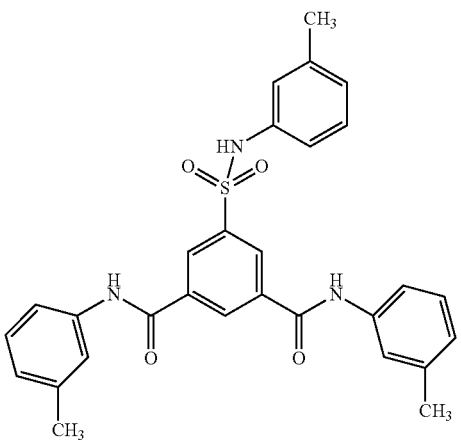

(III)

The compound of formula (I) can exist in different polymorphic forms. In an embodiment, at least two different crystalline polymorphic forms were found for the compound of formula (III), 5-(N-3-methylphenyl-sulfonylamido)-(N',N"-bis-(3-methylphenyl)-isophthalic acid-diamide.

The compound of formula (III) as a crystalline polymorph form a is characterized by an X-ray powder diffraction pattern comprising 2Θ reflections, plus or minus 0.2 degrees 2Θ, at 5.5, 6.1, 6.4, 12.1, 16.1, 16.8, 17.1, 18.3, 19.1, 19.9, 20.2, 21.4, 22.1, 22.7, 23.3, 24.3, 24.7, 25.0, 26.4, 27.7, 29.3; and having a melting point of 211.2° C. (determined using differential scanning colorimetry, DSC).

The compound of formula (III) as a crystalline polymorph form α is characterized by an X-ray powder diffraction pattern comprising 2Θ reflections, plus or minus 0.2 degrees 2Θ, at 6.2, 8.1, 10.1, 11.8, 12.2,13.4, 14.1, 15.3, 16.1,17.2, 18.4, 19.1, 20.6, 21.4, 22.4, 24.5, 25.0, 25.9, 26.2, 26.9, 28.4; and having a melting point of 192.2° C. (measured via DSC).

The compound of formula (III) exists in different crystalline polymorph forms. At least one crystalline polymorph form with a melting range above 200° C. (higher melting crystal form) and at least one crystalline polymorph form with a melting range below 200° C. (lower melting crystal form) have been obtained. The formation of the crystalline polymorph form depends upon the solvent. If toluene, methanol/water or n-heptane is used as solvent, the higher melting crystal-line polymorph form (α) is formed. If methanol and THF is used, the low melting crystalline polymorph form (β) is formed. The recrystallization of the crude product in methanol with a small amount of water provides a mixture of high melting form and low melting form (α+β). The high melting crystalline polymorph form is converted to low melting crystalline polymorph form by the suspension with an appropriate solvent. By a suitable thermal heating and annealing procedure, the low melting crystal form can be converted to one of the higher melting crystal form.

Within the context of the presently claimed invention, the term "alkyl", as used herein, refers to an acyclic saturated aliphatic group, including linear or branched alkyl saturated hydrocarbon radicals, denoted by a general formula $C_nH_{2n+1}$ and wherein n is the number of carbon atoms such as 1, 2, 3, 4, etc.

In a preferred embodiment, the linear $C_1$-$C_{18}$ alkyl is selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl and octadecyl; more preferably selected from the group consisting of methyl, ethyl, propyl, butyl, pentyl, hexyl, heptyl, octyl, nonyl, decyl, undecyl, and dodecyl; even more preferably selected from the group consisting of methyl, ethyl, propyl, butyl, pentyl, hexyl, heptyl and octyl; most preferably selected from the group consisting of methyl, ethyl, propyl, butyl, pentyl and hexyl; and in particular preferably selected from the group consisting of methyl and ethyl.

In a preferred embodiment, the branched $C_1$-$C_{18}$ alkyl is selected from the group consisting of isopropyl, iso-butyl, sec-butyl, tert-butyl, neo-pentyl, tert-amyl, 2-methylpentyl, 2-ethyl-hexyl, 2-propyl-heptyl, 2-butyl-octyl, 2-pentyl-nonyl, 2-hexyl-decyl, iso-hexyl, iso-heptyl, iso-octyl, 1,1,3,3-tetramethylbutyl, iso-nonyl, iso-decyl, iso-dodecyl, iso-tetradecyl, iso-hexadecyl and iso-octadecyl; more preferably selected from the group consisting of isopropyl, iso-butyl, neo-pentyl, 2-ethyl-hexyl, 2-propyl-heptyl, 2-butyl-octyl, iso-hexyl, iso-heptyl, iso-octyl, iso-nonyl, iso-decyl and iso-dodecyl.

In another preferred embodiment, the $C_1$-$C_{18}$ alkyl is substituted with substituents selected from the group consisting of aryl, aryloxy, alkoxy, hydroxy, nitrile and halogen. The substituted $C_1$-$C_{18}$ alkyl is selected from the group consisting of 1-phenylethyl, 2-phenylethyl, 2-phenylpropyl, 2-phenylbutyl, 2-phenoxyethyl, 2-phenoxypropyl, 2-phenoxybutyl, 2-hyxroxyethyl, 2-hydroxypropyl, 2-cyanoethyl, 3-cyanopropyl, 2-chloroethyl, 2-fluoroethyl and 3-fluoropropyl; more preferably 1-phenylethyl, 2-phenylethyl, 2-phenoxyethyl.

In a preferred embodiment, the linear $C_1$-$C_8$ alkyl is selected from the group consisting of methyl, ethyl, propyl, butyl, pentyl, hexyl, heptyl and octyl; more preferably selected from the group consisting of methyl, ethyl, propyl, butyl, pentyl and hexyl; even more preferably selected from the group consisting of methyl, ethyl, propyl and butyl; most preferably selected from the group consisting of methyl and ethyl.

In a preferred embodiment, the branched $C_1$-$C_8$ alkyl is selected from the group consisting of isopropyl, iso-butyl, neo-pentyl and 2-ethyl-hexyl; more preferably selected from the group consisting of isopropyl, iso-butyl and neo-pentyl.

In a preferred embodiment, the alkoxy ($R^{11}O-$) is selected from the group consisting of methoxy, ethoxy, propyloxy, isopropyloxy, n-butyloxy, n-pentyloxy, n-hexyloxy, n-heptyloxy, and n-octyloxy; more preferably selected from the group consisting of methoxy, ethoxy, n-propyloxy, isopropyloxy, n-butyloxy and n-hexyloxy.

In a preferred embodiment, the alkoxy substituted alkyl ($R^{11}O-R^{12}-$) is selected from the group consisting of methoxymethyl, ethoxymethyl, n-propoxymethyl, isopropoxymethyl, n-butyloxymethyl, n-pentyloxymethyl, n-hexyloxymethyl, n-heptyloxymethyl, n-octyloxymethyl, methoxyethyl, ethoxyethyl, n-propoxyethyl, isopropoxyethyl, n-butyloxyethyl, n-pentyloxyethyl, n-hexyloxyethyl, n-heptyloxyethyl, n-octyloxyethyl, 2-methoxyethyl, 3-methoxy-n-propyl, 1-methoxy-2-propyl, 4-methoxy-n-butyl, 5-methoxy-n-pentyl, 6-methoxy-n-hexyl, 7-methoxy-n-heptyl and 8-methoxy-n-octyl; more preferably selected from the group consisting of methoxymethyl, ethoxymethyl and 2-methoxy-ethyl.

In a preferred embodiment, the amine substituted alkyl (($R^{13})_2N-R^{12}$) is selected from the group consisting of 2-(dimethylamino)-methyl, 2-(dimethylamino)-ethyl, 2-(diethylamino)-ethyl, 2-(diisopropylamino)-ethyl, 2-(n-propylamino)-ethyl, 3-(dimethylamino)-propyl and 3-(cyclohexylamino)-propyl; more preferably selected from the group consisting of 2-(dimethylamino)-methyl and 2-(dimethylamino)-ethyl.

In a preferred embodiment, the nitrogen containing 5 or 6 membered ring is selected from the group consisting of pyrrolidine, pyrazolidine, imidazolidine, oxazolidine, isoxazolidine, piperidine, morpholine, and piperazine; more preferably selected from the group consisting of pyrrolidine, piperidine and morpholine.

In another preferred embodiment, the amine substituted alkyl (($R^{13})_2N-R^{12}$) is selected from the group consisting of pyrrolidinyl-ethyl, pyrrolidinyl-n-propyl, pyrrolidinyl-n-butyl, piperidinyl-ethyl, piperidinyl-n-propyl, morpholinyl-ethyl and morpholinyl-n-propyl; more preferably selected from the group consisting of pyrrolidinyl-ethyl, piperidinyl-ethyl and morpholinyl-ethyl.

In a preferred embodiment, the radical of formula (II) is phenyl.

In a preferred embodiment, the radical of formula (II) is m-toluidine.

In a preferred embodiment, the radical of formula (II) is benzyl.

In a preferred embodiment, the radical of formula (II) is selected from the group consisting of 2-methylphenyl, 3-methylphenyl, 4-methylphenyl, 2,4-dimethylphenyl, 3,4-dimethylphenyl, 2,6-dimethylphenyl, 2,3,4-trimethylphenyl, 3,4,5-trimethylphenyl, 3-ethylphenyl, 4-ethylphenyl, 2,6-diethylphenyl, 4-propylphenyl, 4-butylphenyl, 4-pentylphenyl, 4-hexylphenyl, 4-heptylphenyl, 4-octylphenyl, 4-isobutylphenyl, 5,6,7,8-tetrahydro-1-naphthyl and 5,6,7,8-tetrahydro-2-naphthyl.

In a preferred embodiment, the amide $-NH-C(=O)-R^{14}$ is selected from the group consisting of acetamide, propionamide, butyramide, n-pentylamide, n-hexylamide, n-heptylamide and n-octylamide; more preferably selected from the group consisting of acetamide, propionamide and butyramide.

In a preferred embodiment, the amide $-C(=O)-NH-R^{14}$ is selected from the group consisting of $-C(=O)-NH-CH_3$, $-C(=O)-NH-C_2H_5$, $-C(=O)-NH-C_3H_7$, $-C(=O)-NH-C_4H_9$, $-C(=O)-NH-O_5H_{11}$, $-C(=O)-NH-C_6H_{13}$, $-C(=O)-NH-C_7H_{15}$ and $-C(=O)-NH-C_8H_{17}$; more preferably selected from the group consisting of $-C(=O)-NH-CH_3$, $-C(=O)-NH-C_2H_5$ and $-C(=O)-NH-C_3H_7$.

In a preferred embodiment, the ester $-C(=O)OR^{15}$ is selected from the group consisting of methyl ester, ethyl ester, n-propyl ester, n-butyl ester, n-pentyl ester, n-hexyl ester, n-heptyl ester and n-octyl ester; more preferably selected from the group consisting of methyl ester, ethyl ester and n-propyl ester.

In a preferred embodiment, halogen is selected from the group consisting of fluorine, chlorine and bromine; more preferably chlorine.

In a preferred embodiment, $R_2$ and $R_3$, or $R_4$ and $R_5$ or both, or $R_3$ and $R_4$, or $R_5$ and $R_6$ or both, or $R_2$ and $R_3$ as well as $R_5$ and $R_6$ together form a hydrocarbon ring comprising 3 or 4 carbon atoms preferably selected from the group consisting of trimethylene, tetramethylene, propenylene, 2-butenylene and 1,3-butadienylene; more preferably $R_2$ and $R_3$ together form a hydrocarbon ring comprising tetramethylene or $R_2$ and $R_3$ together form a hydrocarbon ring comprising tetramethylene.

In a preferred embodiment, Q is selected from the group consisting of a single bond, methylene, ethylene, —$CH_2$—O—, —$CH_2$—$CH_2$—O—, propylene, butylene, pentylene, hexylene, heptylene, octylene, —C(Et)H—, —C(n-Pr)H—, —C(n-Pr)H—, —C(n-Bu)H—, —C(i-Bu)H—, —C(sec-Bu)H—, —C(tert-Bu)H—, —C(Me)$HCH_2$—, —$CMe_2CH_2$—; more preferably selected from the group consisting of a single bond, methylene, ethylene, —$CH_2$—$CH_2$—O— and —C(Me)H—; and most preferably Q is a single bond.

In second aspect, the invention relates to a process for the preparation of compound of formula (I) comprising the following steps, a. chlorinating a sulfo-isophthalic compound (IVa) with a chlorination agent to obtain an acid chloride of formula (IVb),

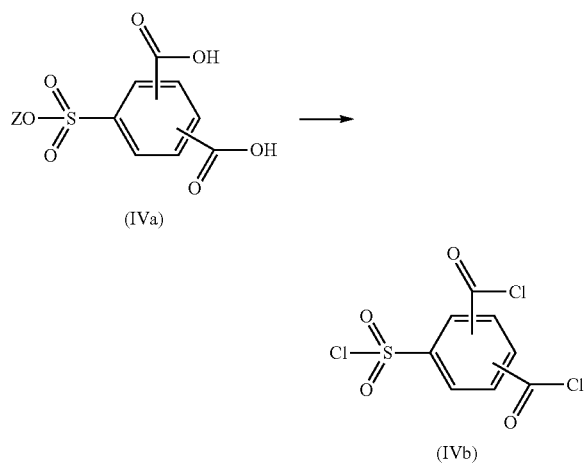

wherein Z stands for hydrogen or an alkali metal, b. optionally isolating the acid chloride (IVb), c. reacting the acid chloride (IVb) with at least one amine to obtain compound of formula (1).

Compounds of formula (IVb) are known in the art and can be prepared according to known methods. In particular, the methods described hereinbelow are used for synthesizing of compounds of formula (IVb).

In a preferred embodiment, the acid chloride of formula (IVb) is 5-sulfonylchloride-isophthalic acid dichloride.

Compounds of formula (IVb) undergo hydrolysis in the presence of water or moisture. As a resuit, the compound (IVb), preferably 5-sulfonyl chloride-isophthalic acid dichloride, is used immediately after its preparation. When storage is required, the acid chloride (IVb), preferably 5-sulfonyl chloride-isophthalic acid dichloride, is stored under anhydrous conditions, for example under an inert atmosphere, and preferably also at a low temperature.

The sulfo-isophthalic compound is represented by the general formula (IVa)

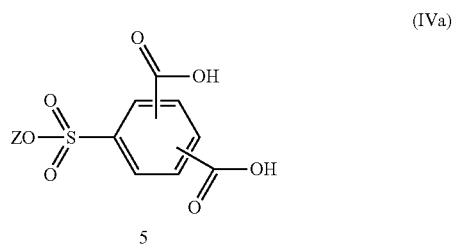

wherein, Z stands for hydrogen or an alkali metal such as sodium or potassium, preferably sodium.

In a preferred embodiment, the compound of formula (IVa) is represented by formula (IV)

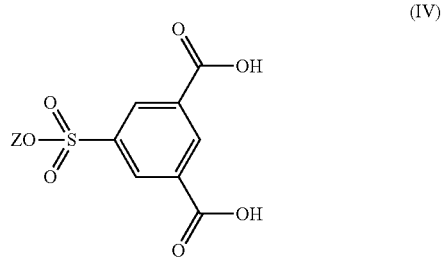

wherein Z stands for hydrogen or an alkali metal such as sodium or potassium, preferably sodium.

In a preferred embodiment, the chlorination agent is selected from the group consisting of thionyl chloride, $POCl_3$, $PCl_5$ and oxalyl chloride.

The amount of the chlorination agent with respect to the compound of formula (IVa) depends upon the chlorination agent. Optionally, a catalyst is used for the chlorination.

$PCl_5$ and $POCl_3$ are highly reactive chlorination agents. In a preferred embodiment, the molar ratio of the highly reactive chlorination agent to the compound of formula (IVa) is in the range of 1:1 to 10:1; more preferably in the range of 1.1:1 to 5:1; most preferably in the range of 1.1:1 to 1.5:1. The highly reactive chlorination agent is preferably used without employing a catalyst.

Thionyl chloride and oxalyl chloride are less reactive chlorination agents. In a preferred embodiment, the molar ratio of the less reactive chlorination agent to the compound of formula (IVa) is in the range of 1:2 to 20:1; in the range of 5:1 to 20:1.

In a particularly preferred embodiment, thionyl chloride is used as a chlorination agent for chlorination of sodium salt of 5-sulfo-isophthalic acid. The molar ratio of the sodium salt of 5-sulfo-isophthalic acid to thionyl chloride is preferably in the range of 1:2 to 1:10; more preferably in the range of 1:2 to 1:5.

In a preferred embodiment, the chlorination is carried out in the presence of a catalyst. The catalyst is preferably selected from the group consisting of dimethylformamide and pyridine.

In a preferred embodiment, the molar amount of the catalyst to compound of formula (IVa) is in the range of 0.01:1 to 2:1; more preferably of 0.1:1 to 0.85:1.

In a particularly preferred embodiment, dimethyl formamide is used as a catalyst in a molar ratio in the range of 0.01:1 to 2:1; more preferably of 0.1:1 to 0.85:1, relative to the sodium salt of 5-sulfo-isophthalic acid.

In a particularly preferred embodiment, the chlorination is carried out using thionyl chloride as a chlorination agent and in the presence of dimethylformamide as a catalyst.

In a preferred embodiment, the chlorination is carried out without the use of a solvent. In another preferred embodiment, the chlorination is carried out in an aprotic aromatic solvent preferably selected from the group consisting of toluene, chlorobenzene and 1,2-dichlorobenzene; more preferably toluene. The weight ratio of the solvent to the compound of formula (IVa) is preferably in the range of 300:1 to 1:1; more preferably of 10:1 to 1:1.

The temperature of chlorination depends upon the reactivity of the chlorination agent and the use of a catalyst.

In a preferred embodiment, the chlorination is carried out at a temperature from 15° C. to the boiling point of the reaction mixture; more preferably 15° C. to 75° C.

In a particularly preferred embodiment, the chlorination is carried out with thionyl chloride as a chlorination agent at ambient pressure under reflux conditions, i.e. between 70 and 75° C.

The reaction time of chlorination depends inter alia upon the reactivity of the chlorination agent, the temperature of chlorination and the use of a catalyst.

The progress of chlorination is monitored by known methods, for example by checking the evolution of hydrogen chloride or sulfur dioxide by well-known methods in the art such as using wetted pH-indicator paper.

In a preferred embodiment, the chlorination reaction time is in the range of 1 to 10 hours; more preferably of 3 to 6 hours.

In a preferred embodiment, the product mixture obtained after chlorination is used as is for the following reaction.

In another preferred embodiment, the product mixture is freeze-dried or stored in an inert atmosphere and preferably, at a low temperature.

In another preferred embodiment, the acid chloride (IVb) is isolated from the product mixture by usual means such as work-up by pouring the product mixture in an ice-water mixture followed by a separation step such filtration, decantation, centrifugation, extraction etc.

In a preferred embodiment, the isolated acid chloride (IVb) is used as is in the following reaction. In another preferred embodiment, the isolated acid chloride (IVb) is freeze-dried or stored in an inert atmosphere and preferably, at a low temperature.

In a particularly preferred embodiment, the product mixture is distilled to remove volatiles and obtain a crude product. During distillation the excess of chlorination agent such as thionyl chloride, the catalyst such as DMF and solvent are distilled off from the product mixture. In a particularly preferred embodiment, the crude acid chloride (IVb) obtained after distillation is used directly for the next step.

In a more preferred embodiment, the product mixture containing acid chloride (IVb) obtained after the chlorination step or the crude acid chloride (IVb) obtained after distillation is subjected to work-up. During work-up, the product mixture is mixed with cold water, or a cold organic solvent such as toluene and tetrahydrofuran. The term 'cold' used in the present context refers to a temperature in the range of (−5) to 10° C. The mixing can be carried out in any order, i.e. by adding product mixture to water or vice versa.

In a particularly preferred embodiment, water having a temperature in the range of 0 and 10° C. or a mixture of ice and water is used for work-up. The weight ratio of water or iced water to compound (IVa) is preferably in the range of 1:1 to 200:1; more preferably 5:1 to 50:1; and most preferably 15:1 to 25:1. During work-up, the addition is carried out slowly in such a way that the temperature of the resultant mixture is maintained at a temperature preferably in the range of 0 and 15° C.; more preferably 0 and 10° C.; and most preferably 0 and 5° C.

The duration of the work-up step depends upon the amount of unreacted chlorination agent present. The duration of the work-up step is preferably in the range of 10 to 180 minutes; more preferably 20 to 120 minutes.

In a preferred embodiment, the acid chloride (IVb) or the product mixture is stored at a temperature in the range of (−30) and 10° C.; more preferably in the range of (−25) and (−10)° C. In a particularly preferred embodiment, the acid chloride (IVb) is stored in "deep-freeze" in a commercially available deep freezer (e.g. Liebherr Comfort GS1663) at a temperature range between (−20) and (−18)° C. Optionally, the acid chloride (IVb) or the product mixture is subjected to a freeze drying step using a freeze-dryer (such as Christ Alpha 2-4 LSC) operating under reduced atmospheric pressure such as in the range of 10 to 0.1 mbar.

Appropriate amines are either commercially available or are synthesized according to known methods such as the reduction of the corresponding nitro compounds.

In a preferred embodiment, the at least one amine is selected from the group consisting of ammonia, linear or branched $C_1$-$C_{18}$-alkylamine, $R^{11}O$—$R^{12}$—$NH_2$, wherein $R^{11}$ and $R^{12}$ are independently linear or branched $C_1$-$C_8$-alkyl, $(R^{13})_2N$—$R^{12}$—$NH_2$, wherein $R^{13}$ is a linear or branched $C_1$-$C_8$-alkyl or together with the nitrogen to which they are attached form a 5 or 6 membered ring, and $R^{12}$ is as defined earlier, and an amine of formula (IIa)

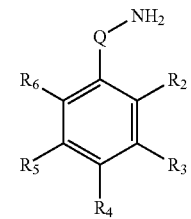

(IIa)

wherein, $R^2$, $R^3$, $R^4$, $R^5$, and $R^6$ are independently selected from the group consisting of hydrogen, linear or branched $C_1$-$C_8$-alkyl, —NH—C(=O)—$R^{14}$, —C(=O)—NH—$R^{14}$, wherein $R^{14}$ is linear or branched $C_1$-$C_8$-alkyl, —C(=O)O$R^{15}$, wherein $R^{15}$ is linear or branched $C_1$-$C_8$-alkyl, and halogen, or $R^2$ and $R^3$, or $R^4$ and $R^5$ or both, or $R^3$ and $R^4$, or $R^5$ and $R^6$ or both, or $R^2$ and $R^3$ as well as $R^5$ and $R^6$ together form a hydrocarbon diradical comprising 3 or 4 carbon atoms;

and

Q is a single bond or branched or unbranched $C_1$-$C_8$-alkylene, optionally comprising one or more oxygen atoms.

In a preferred embodiment, the linear $C_1$-$C_{18}$ alkylamine is selected from the group consisting of methylamine, ethylamine, propylamine, butylamine, pentylamine, hexylamine, heptylamine, octylamine, nonylamine, decylamine, undecylamine, dodecylamine, tridecylamine, tetradecylamine, pentadecylamine, hexadecylamine, heptadecylamine and octadecylamine; more preferably selected from the group consisting of methylamine, ethylamine, propylamine, butylamine, pentylamine, hexylamine, heptylamine, octylamine, nonylamine, decylamine, undecylamine, and dodecylamine; even more preferably selected from the group consisting of methylamine, ethylamine, propylamine, butylamine, pentylamine, hexylamine, heptylamine and octylamine; most preferably selected from the group consisting of methylamine, ethylamine, propylamine, butylamine, pentylamine and hexylamine; and in particular preferably selected from the group consisting of methylamine, ethylamine and propylamine.

In a preferred embodiment, the branched $C_1$-$C_{18}$ alkylamine is selected from the group consisting of isopropylamine, iso-butylamine, sec-butylamine, tert-butylamine, neo-pentylamine, tert-amylamine, 2-methylpentylamine, 2-ethylhexylamine, 2-propyl-heptylamine, 2-butyl-octylamine, 2-pentyl-nonylamine, 2-hexyl-decylamine, iso-hexylamine, iso-heptylamine, iso-octylamine, 1,1,3,3-tetramethylbutylamine, iso-nonylamine, iso-decylamine, iso-dodecylamine, iso-tetradecylamine, iso-hexadecylamine and iso-octadecylamine; more preferably selected from the group consisting of isopropylamine, iso-butylamine, neo-pentylamine, 2-ethyl-hexylamine, 2-propyl-heptylamine, 2-butyl-octylamine, iso-hexylamine, iso-heptylamine, iso-octylamine, iso-nonylamine, iso-decylamine and iso-dodecylamine.

In another preferred embodiment, the $C_1$-$C_{18}$ alkylamine is substituted with substituents selected from the group consisting of aryl, aryloxy, alkoxy, hydroxy, nitrile and halogen. The substituted $C_1$-$C_{18}$ alkylamine is selected from the group consisting of 1-phenylethylamine, 2-phenylethylamine, 2-phenylpropylamine, 2-phenylbutylamine, 2-phenoxyethylamine, 2-phenoxypropylamine, 2-phenoxybutylamine, 2-hyxroxyethylamine, 2-hydroxypropylamine, 2-cyanoethylamine, 3-cyanopropylamine, 2-chloroethylamine, 2-fluoroethylamine and 3-fluoropropylamine; more preferably 1-phenylethylamine, 2-phenylethylamine, 2-phenoxyethylamine.

In a preferred embodiment, the linear $C_1$-$C_8$ alkyl is selected from the group consisting of methyl, ethyl, propyl, butyl, pentyl, hexyl, heptyl and octyl; more preferably selected from the group consisting of methyl, ethyl, propyl, butyl, pentyl and hexyl; even more preferably selected from the group consisting of methyl, ethyl, propyl and butyl; most preferably selected from the group consisting of methyl and ethyl.

In a preferred embodiment, the branched $C_1$-$C_8$ alkyl is selected from the group consisting of isopropyl, iso-butyl, neo-pentyl and 2-ethyl-hexyl; more preferably selected from the group consisting of isopropyl, iso-butyl and neo-pentyl.

In a preferred embodiment, the alkoxyamine is selected from the group consisting of methoxyamine, ethoxyamine, propyloxyamine, isopropyloxyamine, n-butyloxyamine, n-pentyloxyamine, n-hexyloxyamine, n-heptyloxyamine, and n-octyloxyamine; more preferably selected from the group consisting of methoxyamine, ethoxyamine, n-propyloxyamine, isopropyloxyamine, n-butyloxyamine and n-hexyloxyamine.

In a preferred embodiment, the alkoxy alkylamine ($R^{11}O$—$R^{12}$—$NH_2$) is selected from the group consisting of methoxymethylamine, ethoxymethylamine, n-propoxymethylamine, isopropoxymethylamine, n-butyloxymethylamine, n-pentyloxymethylamine, n-hexyloxymethylamine, n-heptyloxymethylamine, n-octyloxymethylamine, methoxyethylamine, n-pentyloxyethylamine, n-hexyloxyethylamine, n-heptyloxyethylamine, n-octyloxyethylamine, n-pentyloxyethylamine, 3-methoxy-n-propylamine, 1-methoxy-2-propylamine, 4-methoxy-n-butylamine, 5-methoxy-n-pentylamine, 6-methoxy-n-hexylamine, 7-methoxy-n-heptylamine and 8-methoxy-n-octylamine; more preferably selected from the group consisting of methoxymethylamine, ethoxymethylamine and 2-methoxyethylamine.

In a preferred embodiment, the amine substituted alkylamine (($R^{13}$)$_2$N—$R^{12}NH_2$) is selected from the group consisting of 2-(dimethylamino)-methylamine, 2-(dimethylamino)-ethylamine, 2-(diethylamino)-ethylamine, 2-(diisoprobylamino)-ethylamine, 2-(n-propylamino)-ethylamine, 3-(dimethylamino)-propylamine and 3-(cyclohexylamino)-propylamine; more preferably selected from the group consisting of 2-(dimethylamino)-methylamine and 2-(dimethylamino)-ethylamine.

In a preferred embodiment, the nitrogen containing 5 or 6 membered ring is selected from the group consisting of pyrrolidine, pyrazolidine, imidazolidine, oxazolidine, isooxazolidine, piperidine, morpholine, and piperazine; more preferably selected from the group consisting of pyrrolidine, piperidine and morpholine.

In another preferred embodiment, the amine substituted alkylamine (($R^{13}$)$_2$N—$R^{12}NH_2$) is selected from the group consisting of pyrrolidinyl-ethylamine, pyrrolidinyl-n-propylamine, pyrrolidinyl-n-butylamine, piperidinyl-ethylamine, piperidinyl-n-propylamine, morpholinyl-ethylamine and morpholinyl-n-propylamine; more preferably selected from the group consisting of pyrrolidinyl-ethylamine, pyrrolidinyl-n-propylamine, piperidinyl-ethylamine, piperidinyl-n-propylamine, morpholinyl-ethylamine and morpholinyl-n-propylamine.

In a preferred embodiment, the amine of formula (IIa) is selected from the group consisting of o-toluidine, m-toluidine, p-toluidine, 2,4-dimethylaniline, 3,4-dimethylaniline, 2,6-dimethylaniline, 2,3,4-trimethylaniline, 3,4,5-trimethylaniline, 3-ethylaniline, 4-ethylaniline, 2,6-diethylaniline, 4-propylaniline, 4-butylaniline, 4-pentylaniline, 4-hexylaniline, 4-heptylaniline, 4-octylaniline, 4-isobutylaniline, 5,6,7,8-tetrahydro-1-naphthylamine and 5,6,7,8-tetrahydro-2-naphthylamine.

In a preferred embodiment, the amine of formula (IIa) is aniline.

In a preferred embodiment, the amine of formula (IIa) is m-toluidine.

In a preferred embodiment, the amine of formula (IIa) is benzylamine.

In a preferred embodiment, the amide —NH—C(=O)—$R^{14}$ is selected from the group consisting of acetamide, propionamide, butyramide, n-pentylamide, n-hexylamide, n-heptylamide and n-octylamide; more preferably selected from the group consisting of acetamide, propionamide and butyramide.

In a preferred embodiment, the amide —C(=O)—NH—$R^{14}$ is selected from the group consisting of —C(=O)—NH—$CH_3$, —C(=O)—NH—$C_2H_5$, —C(=O)—NH—$C_3H_7$, —C(=O)—NH—$C_4H_9$, —C(=O)—NH—$O_5H_{11}$, —C(=O)—NH—$C_6H_{13}$, —C(=O)—NH—$C_7H_{15}$ and —C(=O)—NH—$C_8H_{17}$; more preferably selected from the group consisting of —C(=O)—NH—$CH_3$, —C(=O)—NH—$C_2H_5$ and —C(=O)—NH—$C_3H_7$.

In a preferred embodiment, the amine of formula (IIa) is 4-acetamidoaniline.

In a preferred embodiment, the ester —C(=O)OR$^{15}$ is selected from the group consisting of methyl ester, ethyl ester, n-propyl ester, n-butyl ester, n-penyl ester, n-hexyl ester, n-heptyl ester and n-octyl ester; more preferably selected from the group consisting of methyl ester, ethyl ester and n-propyl ester.

In a preferred embodiment, halogen is selected from the group consisting of fluorine, chlorine and bromine; more preferably chlorine.

In a preferred embodiment, $R_2$ and $R_3$, or $R_4$ and $R_5$ or both, or $R_3$ and $R_4$, or $R_5$ and $R_6$ or both, or $R_2$ and $R_3$ as well as $R_5$ and $R_6$ together form a hydrocarbon ring comprising 3 or 4 carbon atoms preferably selected from the group consisting of trimethylene, tetramethylene, propenylene, 2-butenylene and 1,3-butadienylene; more preferably $R_2$ and $R_3$ together form a hydrocarbon ring comprising tetramethylene or $R_2$ and $R_3$ together form a hydrocarbon ring comprising tetramethylene.

In a preferred embodiment, Q is selected from the group consisting of a single bond, methylene, ethylene, —CH$_2$—O—, —CH$_2$—CH$_2$—O—, propylene, butylene, pentylene, hexylene, heptylene, octylene, —C(Et)H—, —C(n-Pr)H—, —C(i-Pr)H—, —C(n-Bu)H—, —C(i-Bu)H—, —C(sec-Bu)H—, —C(tert-Bu)H—, —C(Me)HCH$_2$—, —CMe$_2$CH$_2$—; more preferably selected from the group consisting of a single bond, methylene, ethylene-CH$_2$—CH$_2$—O— and —C(Me)H—; and most preferably Q is a single bond.

In a particularly preferred embodiment, the amine is selected from the group consisting of benzylamine, aniline, m-toluidine, n-butylamine, 1-phenylethylamine, 2-phenylethylamine, 2-methoxyethylamine, n-octylamine, 2,6-diethylaniline, n-octylamine, 2-phenoxyethylamine.

In a preferred embodiment, the molar ratio of the amine to the acid chloride (IVb) is in the range of 1:1 to 10:1.

In a preferred embodiment, the reaction of the acid chloride (IVb) and the amine (IIa) is performed without a solvent. In another preferred embodiment, the reaction is performed in a solvent. The weight ratio of the solvent to the acid chloride (IVb) is preferably in the range of 5:1 to 25:1; more preferably 1:1 to 25:1; even more preferably 1:1 to 20:1.

In a preferred embodiment, the solvent is selected from aprotic polar solvents such as dimethyl-formamide, dimethylamine and N-methylpyrrolidone, linear or cyclic ethers such as tetrahydrofuran, propyleneglycol-dimethylether and anisole, non-polar solvents such as alkanes like n-heptane, aromatic solvents such as toluene and xylene, and protic polar solvents such as water and alcohols. The alcohol is preferably a C$_1$-C$_4$-alkanol such as methanol, ethanol, n-propanol, isopropanol and n-butanol. In a more preferred embodiment, the solvent is selected from aprotic polar solvents and non-polar solvents.

In a preferred embodiment, the reaction of the acid chloride (IVb) with the amine (IIa) is per-formed as an interfacial reaction or a biphasic process using an organic solvent and water. Optionally, the reaction is performed in the presence of a base. The acid chloride is dissolved in an organic solvent and is added to an aqueous solution of the amine and optionally, an inorganic base.

In a preferred embodiment, the base selected from the group consisting of inorganic bases and organic bases. The inorganic base is preferably selected from the group consisting of alkali metal hydroxides, earth alkali metal hydroxides, earth alkali metal carbonates and earth alkali metal bicarbonates such as NaOH, KOH, Ca(OH)$_2$, NaHCO$_3$ and CaCO$_3$. The organic base is preferably selected from the group consisting of triethylamine and diisopropylethylamine. The molar ratio of the additional base to the first amine R$^1$NH$_2$ is preferably in the range of from 1:1 to 10:1. The inorganic base is preferably selected from the group consisting of NaHCO$_3$ and CaCO$_3$; more preferably NaHCO$_3$.

In a preferred embodiment, the molar ratio of the amine to the acid chloride is in the range of 1:1 to 10:1, more preferably 3:1 to 8:1, when the reaction is performed without a base. The molar ratio of the amine to the acid chloride is in the range of 1:1 to 2:1, when the reaction is carried out in the presence of a base.

In a preferred embodiment, the biphasic process for reaction of the acid chloride (IVb) with the amine (IIa) is performed in the presence of a surfactant. The surfactant is preferably a nonionic dynamic wetting agent such as tetramethyldecynediol, gemini surfactant.

The reaction temperature depends on the reactivity of the amine. In a preferred embodiment, the reaction is performed at a temperature in the range of 0 and 100° C.

In a particularly preferred embodiment, the solvent is water or t-butyl-methyl ether and the reaction temperature is in the range of 0 to 25° C.; the molar ratio of the amine to the acid chloride (IVb) is in the range of 1:1 to 10:1, more preferably 4:1 to 8:1; and the weight ratio of the solvent to the acid chloride (IVb) is in the range of 1:1 to 25:1, more preferably 2:1 to 20:1.

In a particularly preferred embodiment, the solvent is a non-polar solvent such as toluene and the reaction temperature is in the range of 20 to 100° C.; the molar ratio of the amine to the acid chloride (IVb) is in the range of 1:1 to 10:1, more preferably 4:1 to 8:1, and the weight ratio of the solvent to the acid chloride (IVb) is in the range of 1:1 to 25:1, more preferably of 2:1 to 20:1.

In a particularly preferred embodiment, the solvent is ethanol and the reaction temperature is in the range of 0 to 100° C., and the molar ratio of the amine to the acid chloride (IVb) is in the range of 1:1 to 10:1, more preferably 4:1 to 8:1; and the weight ratio of the solvent to the acid chloride (IVb) is in the range of 1:1 to 25:1, more preferably 2:1 to 20:1.

In a preferred embodiment, the compound of formula (I) obtained by amination of acid chloride is isolated by work-up or by known methods such as filtration, decantation, centrifugation, and optionally further procedures such as a washing step or (re-)crystallization.

In a preferred embodiment, the washing step is performed with water or acidified water, for example water acidified with an inorganic acid such as hydrochloride acid. The acidified water preferably has a pH in the range of 1 to 5.

The reactivity of the two carbonyl chloride groups of the acid chloride of formula (IVb) is higher as compared to the sulfonyl chloride group. As a consequence, it is possible to synthesize compound of formula (I) having different R and R$_1$ groups by first reacting the acid chloride (IVb) with a first amine R$_1$NH$_2$ to obtain a diamide intermediate, followed by its reaction with a second amine RN H$_2$.

In a preferred embodiment, to prepare compound of formula (I) having different R and R$^1$, the step of reacting the acid chloride (IVb) with at least one amine comprises the following sub-steps, i. reacting an acid chloride of formula (IVb) with a first amine R$^1$NH$_2$ to obtain compound of formula (V),

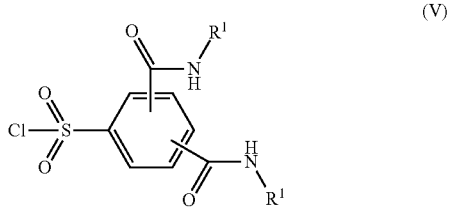

(V)

ii. reacting the product obtained in substep i. with a second amine RNH₂ to obtain compound of formula (I) wherein R and R¹ are different.

The first amine R¹NH₂ and the second amine RNH₂ are the same as the amines described earlier.

In a particularly preferred embodiment, the compound of formula (IVb) is 5-sulfonyl chloride-isophthalic acid dichloride and the compound of formula (V) is (Va).

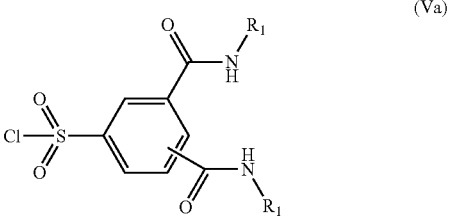

(Va)

In a particularly preferred embodiment, the combination of first amine R¹NH₂ and second amine RNH₂ is selected from the group consisting of benzylamine and aniline, aniline and benzylamine, benzylamine and toluidine, n-butylamine and toluidine, 1-phenylethylamine and toluidine, 2-phenylethylamine and toluidine, 2-methoxyethylamine and toluidine, n-octylamine and toluidine, benzylamine and 2,6-diethylaniline, n-octylamine and 2,6-diethylaniline, and 2-phenoxyethylamine and 2,6-diethylaniline.

In a preferred embodiment, the molar ratio of the acid chloride (IVb) to the first amine R¹NH₂ is preferably in the range of 0.05:1 to 1:1; more preferably of 0.1:1 to 0.4:1.

In a preferred embodiment, the reaction of the acid chloride (IVb) to the amine is performed using an additional base selected from the group consisting of inorganic bases and organic bases. The inorganic base is preferably selected from the group consisting of alkali metal hydroxides, earth alkali metal hydroxides, earth alkali metal carbonates and earth alkali metal bicarbonates such as NaOH, KOH, Ca(OH)₂, NaHCO₃ and CaCO₃. The organic base is preferably selected from the group consisting of triethylamine and diisopropylethylamine. The molar ratio of the additional base to the first amine R¹NH₂ is preferably in the range of from 1:1 to 10:1. The inorganic base is preferably selected from the group consisting of NaHCO₃ and CaCO₃; more preferably NaHCO₃.

In a preferred embodiment, the molar ratio of the compound (V) to the second amine RNH₂ is in the range of 0.1:1 to 1:1; more preferably 0.1:1 to 0.5:1.

Substeps (i) and (ii) are carried out in a similar manner to the reaction of the acid chloride (IVb) with amine (IIa) described earlier.

In an embodiment, the substep (i) is performed at a temperature in the range of 60 to 100° C.; more preferably 80 to 100° C.; and the molar ratio of the acid chloride (IVb) to the first amine R₁NH₂ is in the range of 0.1:1 to 1:1, more preferably of 0.2:1 to 0.5:1.

In another embodiment, the substep (i) is performed at a temperature in the range of 20 to 60° C.; and the molar ratio of the acid chloride (IVb) to the first amine R₁NH₂ is in the range of 0.05:1 to 1:1; more preferably of 0.1:1 to 0.4:1.

In a preferred embodiment, the reaction time for substep (i) is in the range of 1 to 10 hours; more preferably 2 to 7 hours. In a preferred embodiment, the reaction time for substep (ii) is in the range of 1 to 24 hours; more preferably 2 to 20 hours.

The reaction mixture is worked up by known methods, for example those mentioned above.

In third aspect, the presently claimed invention is directed to the use of compound (I) as color developer in a heat sensitive recording material.

In fourth aspect, the presently claimed invention is directed to a heat sensitive recording material comprising
A) at least one color former, and
B) at least one color developer of formula (I)

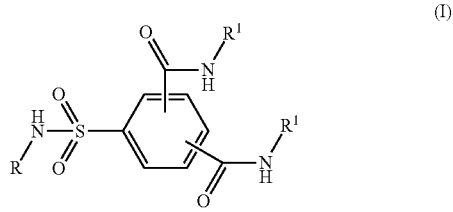

(I)

wherein R and R¹ are defined as defined earlier.

In a preferred embodiment, the weight ratio of color developer to color former is in the range of 1.5:1 to 3:1.

The methods for manufacturing heat sensitive recording material are well known in the art. For example, at least one color former and at least one color developer, optionally at least one sensitizer, optionally at least one stabilizer and optionally at least one pigment are milled separately in water or a compound with dispersing capabilities by means of a mill such as a bead mill, an attritor, a sand mill or like milling apparatus to form a fine particle dispersion with an average particle diameter preferably in the range of 0.1 to 2.0 μm; more preferably of 0.3 to 1.0 μm.

In a preferred embodiment, the compound with dispersing capabilities is at least one selected from the group consisting of water-soluble polymer, anionic surfactant and non-ionic surfactant. The water-soluble polymer is preferably selected from the group consisting of polyvinyl alcohol, carboxylic acid-modified polyvinyl alcohol, sulfonic acid-modified polyvinyl alcohol, methyl cellulose, hydroxypropyl cellulose and hydroxypropylmethyl cellulose. The anionic surfactant is preferably selected from the group consisting of sodium salt of sulfonated naphthalene-formaldehyde condensation product, polyoxyethylene alkyl ether sulfuric acid ester salt and di-alkylsulfosuccinic acid ester sodium salt. The nonionic surfactant is preferably selected from the group consisting of polyoxyethylene alkyl ether and polyoxyethylene sorbitan fatty acid ester. In a most preferred embodiment, the compound with dispersing capabilities is at least one selected from polyvinyl alcohol, sulfonic acid-modified polyvinyl alcohol and methyl cellulose.

The fine particle dispersion is combined with conventional amounts of additives selected from the group consisting of binders, pigments and lubricants; and the resulting mixture is stirred to obtain a heat sensitive recording layer composition. The composition optionally contains a stabilizer and/or one or more auxiliaries. The heat sensitive recording material composition is applied to a support and the resulting coating is dried to obtain a support coated with a heat sensitive recording layer. The heat sensitive recording layer is also referred to as thermal layer.

The heat sensitive recording material of the presently claimed invention is useful for other end use applications that employ color forming materials, for example, a temperature indicating material.

The support is selected from a variety of suitable supports used in this field. In a preferred embodiment, the support is selected from the group consisting of paper, wood-free paper made from non-chlorine bleached pulp, base paper containing waste paper plastic films and synthetic paper.

In a preferred embodiment, the amount of the at least one color former is in the range of 5 to 15% by weight, based on dry weight of the heat sensitive recording layer.

In a preferred embodiment, the amount of the at least one color developer is in the range of 10 to 50% by weight, based on dry weight of the heat sensitive recording layer.

In a preferred embodiment, the heat sensitive recording layer further comprises at least one sensitizer.

In a particularly preferred embodiment, the heat sensitive recording layer comprises 3-dibutylamino-6-methyl-7-anilnofluoran as a color former, 5-(N-3-methylphenyl-sulfonylamido)-(N',N''-bis-(3-methylphenyl)-isophthalic acid-diamide as a color developer and benzyl-2-naphthyl ether as a sensitizer.

In a preferred embodiment, the amount of the at least one sensitizer is in the range of 10 to 50% by weight, based on dry weight of the heat sensitive recording layer.

In a preferred embodiment, the weight ratio of color developer to sensitizer is in the range of 0.5:1 to 1.5:1.

In a preferred embodiment, the heat sensitive recording layer further comprises at least one stabilizer.

In a particularly preferred embodiment, the heat sensitive recording layer comprises 3-dibutylamino-6-methyl-7-anilinofluoran as a color former, 5-(N-3-methylphenyl-sulfonylamido)-(N',N''-bis-(3-methylphenyl)-isophthalic acid-diamide as a color developer, and carbamic acid, N,N-[sulfonylbis[4,1-phenyleneiminocarbonylimino(methylphenylene]] bis-C,C-diphenyl ester as a stabilizer.

In a particularly preferred embodiment, the heat sensitive recording layer comprises 3-dibutylamino-6-methyl-7-anilnofluoran as a color former, 5-(N-3-methylphenyl-sulfonylamido)-(N',N''-bis-(3-methylphenyl)-isophthalic acid-diamide as a color developer, benzyl-2-naphthyl ether as a sensitizer and carbamic acid, N,N-[sulfonylbis[4,1-phenyleneiminocarbonylimino(methylphenylene]]bis-C,C-diphenyl ester as a stabilizer.

In a preferred embodiment, the amount of the at least one stabilizer is in the range of 5 to 20% by weight, based on dry weight of the heat sensitive recording layer.

In a preferred embodiment, the at least one color former is selected from the group consisting of triphenylmethane, lactone and fluoran.

In a preferred embodiment, the at least one color former is selected from the group consisting of 3-diethylamino-6-methylfluoran, 3-dimethylamino-6-methyl-7-anilinofluoran, 3-diethylamino-6-methyl-7-anilinofluoran, 3-diethylamino-6-methyl-7-(2,4-dimethylanilino) fluoran, 3-diethylamino-6-methyl-7-chlorofluoran, 3-diethylamino-6-methyl-7-(3-trifluoromethylanilino) fluoran, 3-diethylamino-6-methyl-7-(2-chloroanilino) fluoran, 3-diethylamino-6-methyl-7-(4-chloroanilino) fluoran, 3-diethylamino-6-methyl-7-(2-fluoroanilino) fluoran, 3-diethylamino-6-methyl-7-(4-n-octylanilino) fluoran, 3-diethylamino -7-(4-n-octylanilino) fluoran, 3-diethylamino -7-(n-octylamino) fluoran, 3-diethylamino -7-(dibenzylamino) fluoran, 3-diethylamino-6-methyl-7-(dibenzylamino) fluoran, 3-diethylamino-6-chloro-7-methylfluoran, 3-diethylamino-7-t-butylfluoran, 3-diethylamino -7-carboxyethylfluoran, 3-diethylamino-6-chloro-7-anilinofluoran, 3-diethylamino-6-methyl-7-(3-methylanilino) fluoran, 3-diethylamino-6-methyl-7-(4-methylanilino) fluoran, 3-diethylamino-6-ethoxyethyl-7-anilinofluoran, 3-diethylamino-7-methylfluoran, 3-diethylamino-7-chlorofluoran, 3-diethylamino-7-(3-trifluoromethylanilino) fluoran, 3-diethylamino-7-(2-chloroanilino) fluoran, 3-diethylamino-7-(2-fluoroanilino) fluoran, 3-diethylamino-benzo[a]fluoran, 3-diethylamino-benzo[c]fluoran, 3-dibutylamino-7-dibenzylaminofluoran, 3-dibutylamino-7-anilinofluoran , 3-diethylamino-7-anilinofluoran, 3-dibutylamino-6-methyl fluoran, 3-dibutylamino-6-methyl-7-anilinofluoran, 3-dibutylamino-6-methyl-7-(2,4-dimethylanilino) fluoran, 3-dibutylamino-6-methyl-7-(2-chloroanilino) fluoran, 3-dibutylamino-6-methyl-7-(4-chloroanilino) fluoran, 3-dibutylamino-6-methyl-7-(2-fluoroanilino) fluoran, 3-dibutylamino-6-methyl-7-(3-trifluoromethylanilino) fluoran, 3-dibutylamino-6-ethoxyethyl-7-anilinofluoran, 3-dibutylamino-6-chloroanilinofluoran, 3-dibutylamino-6-methyl-7-(4-methylanilino) fluoran, 3-dibutylamino-7-(2-chloroanilino) fluoran, 3-dibutylamino-7-(2-fluoroanilino) fluoran, 3-dibutylamino-7-(N-methyl-N-formylamino) fluoran, 3-dipentylamino-6-methyl-7-anilinofluoran, 3-dipentylamino-6-methyl-7-(2-chloroanilino) fluoran, 3-dipentylamino-7-(3-trifluoromethylanilino) fluoran, 3-dipentylamino-6-chloro-7-anilinofluoran, 3-dipentylamino-7-(4-chloroanilino) fluoran, 3-pyrrolidino-6-methyl-7-anilinofluoran, 3-piperidino-6-methyl-7-anilinofluoran, 3-(N-methyl-N-propylamino)-6-methyl-7-anilinofluoran, 3-(N-methyl-N-cyclohexylamino)-6-methyl-7-anilinofluoran, 3-(N-ethyl-N-cyclohexylamino)-6-methyl-7-anilinofluoran, 3-(N-ethyl-p-toluidino)-6-methyl-7-anilinofluoran, 3-(N-ethyl-N-isoamylamino)-6-methyl-7-anilinofluoran, 3-(N-ethyl-N-isoamylamino)-6-chloro-7-anilinofluoran, 3-(N-ethyl-N-tetrahydrofurfurylamino)-6-methyl-7-anilinofluoran, 3-(N-ethyl-N-isobutylamino)-6-methyl-7-anilinofluoran, 3-(N-butyl-N-isoamylamino)-6-methyl-7-anilinofluoran, 3-(N-isopropyl-N-3-pentylamino)-6-methyl-7-anilinofluoran, 3-(N-ethyl-N-ethoxypropylamino)-6-methyl-7-anilinofluoran, 3-cyclohexylamino-6-chlorofluoran, 2-methyl-6-p-(p-dimethylaminophenyl)aminoanilinofluoran, 2-methoxy-6-p-(p-dimethylaminophenyl)-aminoanilinofluoran, 2-chloro-3-methyl-6-p-(p-phenylaminophenyl)aminoanilinofluoran, 2-diethylamino-6-p-(p-dimethylaminophenyl)aminoanilinofluoran, 2-phenyl-6-methyl-6-p-(p-phenylaminophenyl)aminoanilinofluoran, 2-benzyl-6-p-(p-phenylaminophenyl)amino-anilinofluoran, 3-methyl-6-p-(p-dimethylaminophenyl)aminoanilinofluoran, 3-diethylamino-6-p-(p-diethylaminophenyl)aminoanilinofluoran, 3-diethylamino-6-p-(p-dibutylaminophenyl)-aminoanilinofluoran, 2,4-dimethyl-6-[(4-dimethylamino)anilino] fluoran, 3-[(4-dimethyl-aminophenyl)amino]-5,7-dimethylfluoran, 3,6,6'-tris(dimethylamino)spiro[fluorene-9,3'-phthalide], 3,6,6'-tris(diethylamino)spiro[fluorene-9,3'-phthalide], 3,3-bis(p-dimethylamino-phenyl)-6-dimethylaminophthalide, 3,3-bis(p-dimethylaminophenyl) phthalide, 3,3-bis-[2-(p-dimethylaminophenyl)-2-(p-methoxyphenyl)ethenyl-4,5,6,7-tetrabromophthalide, 3,3-bis-[2-(p-dimethylaminophenyl)-2-(p-methoxyphenyl) ethenyl-4,5,6,7-tetrachlorophthalide, 3,3-bis[1,1-bis(4- pyrrolidinophenyl)ethylene-2-yl]-4,5,6,7-tetrabromophthalide, 3,3-bis-[1-(4-methoxyphenyl)-1-(4-pyrridinophenyl)ethylene-2-yl]-4,5,6,7-tetrachlorophthalide, 3-(4-diethylamino-2-ethoxyphenyl)-3-(1-ethyl-2-methylindole-3-y0-4-azaphthalide, 3-(4-diethylamino-2-ethoxyphenyl)-3-(1-octyl-2-methylindole-3-yl)-4-azaphthalide, 3-(4-cyclohexylethylamino-2-methoxyphenyl)-3-(1-ethyl-2-methylindole-3-yl)-4-azaphthalide, 3,3-bis(1-ethyl-2-methylindole-3-yl) phthalide, 3,3-bis(1-octyl-2-methylindole-3-yl) phthalide, 3-diethylamino-6,8-dimethylfluoran, 3-diethylamino-7,8-benzofluoran, 3-diethylaminofluoran-7-carboxylic acid ethyl ester and 3-[N-(4-methylphenyl)-N-ethylamino]-7-methylfluoran.

All of the above color formers are used either singly or as a mixture with other color formers; or they are used together with further black color forming compounds.

In a more preferred embodiment, the at least one color former is selected from group consisting of 3-dibutylamino-6-methyl-7-anilinofluoran, 3-dipentylamino-6-methyl-7-anilinofluoran, 3-(N-ethyl-N-isoamylamino)-6-methyl-7-anilinofluoran and 3-N-ethyl-p-toluidino-6-methyl-7-anilinofluoran.

In a particularly preferred embodiment, the at least one color former is a mixture of 3-dibutylamino-6-methyl-7-anilinofluoran and 3-(N-ethyl-N-isoamylamino)-6-methyl-7-anilinofluoran.

Optionally, the heat sensitive recording layer contains an additional color developer selected from previously known color developers, unless the color forming performance of the resultant heat sensitive recording material is disturbed thereby. Such a color developer is selected from the group consisting of 4,4'-isopropylidene bisphenol, 4,4'-sec-butylidene bisphenol, 4,4'-cyclohexylidene bisphenol, 2,2-bis-(4-hydroxyphenyl)-4-methylpentane, 2,2-dimethyl-3,3-di(4-hydroxyphenyl)butane, 2,2'-dihydroxydiphenyl, 1-phenyl-1,1-bis(4-hydroxyphenyl)butane, 4-phenyl-2,2-bis(4-hydroxyphenyl)butane, 1-phenyl-2,2-bis(4-hydroxyphenyl)butane, 2,2-bis(4'-hydroxy-3'-methylphenyl)-4-methylpentane, 2,2-bis(4'-hydroxy-3'-tert-butyllphenyl)-4-methylpentane, 4,4'-sec-butylidene-bis (2-methylphenol), 4,4'-isopropylidene-bis (2-tert-butylphenol), 2,2-bis(4'-hydroxy-3'-isopropylphenyl)-4-methylpentane, allyl-4,4-bis (4'-hydroxyphenyl) pentanoate, propargyl-4,4-bis(4'-hydroxyphenyl) pentanoate, n-propyl-4,4-bis (4'-hydroxyphenyl) pentanoate, 2,4-bis (phenylsulfonyl) phenol, 2-(4-methylsulfonyl)-4-(phenylsulfonyl) phenol, 2-(phenylsulfonyl)-4-(4-methylsulfonyl) phenol, 2,4-bis (4-methylphenylsulfonyl) phenol, pentamethylene-bis(4-hydroxybenzoate), 2,2-dimethyl-3,3-di(4-hydroxyphenyl)pentane, 2,2-di(4-hydroxyphenyl)hexane, 4,4'-dihydroxydiphenyl thioether, 1,7-di(4-hydroxyphenylthio)-3,5-dioxaheptane, 2,2'-bis(4-hydroxyphenylthio)diethyl ether, 4,4'-dihydroxy-3,3'-dimethylphenyl thioether; benzyl-4-hydroxybenzoate, ethyl-4-hydroxybenzoate, propyl-4-hydroxybenzoate, isopropyl-4-hydroxybenzoate, butyl-4-hydroxybenzoate, isobutyl-4-hydroxybenzoate, 4,4'-dihydroxydiphenyl sulfone, 2,4'-dihydroxydiphenyl sulfone, 4-hydroxy-4'-methyldiphenyl sulfone, 4-hydroxy-4'-isopropoxydiphenyl sulfone, 4-hydroxy-4'-butoxydiphenyl sulfone, 4-hydroxy-4'-benzyloxydiphenyl sulfone, 4,4'-dihydroxy-3,3'-diallyldiphenyl sulfone, 4-[[4-(2-propenyl-1-yloxy)phenol]sulfonyl phenol, 3,4-dihydroxy-4'-methyldiphenyl sulfone, 4,4'-dihydroxy-3,3',5,5'-tetrabromodiphenyl sulfone, 4,4'-bis (p-toluenesulphonylamino-carbonylamino) diphenylmethane, N-p-toluenesulphonyl-M-phenyl urea, N-p-toluenesulfonyl-N'-3-(p-toluenesulfonyloxy)phenylurea, N-[2-(3-phenylureido)phenyl] benzenesulfonamide, N-phenyl-N'-[phenylamino)sulfonyl]urea, N-(4-methylphenyl)-N-[[4-methylphenyl)amino]sulfonyl]urea, N-[(phenylamino)sulfonyl]benzamide, dimethyl 4-hydroxyphthalate, dicyclohexyl 4-hydroxyphthalate, diphenyl 4-hydroxyphthalate, 4-[2-(4-methoxyphenyloxy)ethyloxy] salicylate, 3,5-di-tert-butylsalicylic acid, 3-benzyl salicylic acid, 3-(α-methylbenzyl) salicylic acid, 3-phenyl-5-(α,α-dimethylbenzyl) salicylic acid, 3,5-di-α-methylbenzyl salicylic acid; metal salts of salicylic acid, 2-benzylsulfonyl-benzoic acid, 3-cyclohexyl-4-hydroxybenzoic acid, zinc benzoate, zinc 4-nitrobenzoate, 4-(4'-phenoxy-butoxy) phthalic acid, 4-(2'-phenoxyethoxy)phthalic acid, 4-(3'-phenylpropyloxy)phthalic acid, mono (2-hydroxyethyl) -5-nitro-isophthalic acid, 5-benzyloxycarbonyl isophthalic acid, 5-(1'-phenylethanesulfonyl) isophthalic acid, bis(1,2-dihydro-1,5-dimethyl-2-phenyl-3H-pyrazol-3-one-O)bis(thiocyanato-N) zinc, and mixtures thereof.

In a preferred embodiment, the at least one sensitizer is selected from the group consisting of stearamide, methylol stearamide, methylene bis-stearamide, ethylene bis-stearamide, amide waxes, p-benzylbiphenyl, m-terphenyl, benzyl-2-naphthyl ether, 4-methoxybiphenyl, bis(p-tolylmethyl)oxalate, dibenzyl oxalate, di(4-methylbenzyl) oxalate, di(4-chlorobenzyl) oxalate, diphenyl sulfone, dimethyl terephthalate, dibenzyl terephthalate, dibenzyl isophthalate, 1,2-diphenoxyethane, 1,2-bis(4-methylphenoxy) ethane, 1,2-bis(3-methylphenoxy) ethane, 4,4'-dimethylbiphenyl, phenyl-1-hydroxy-2-naphthoate, 4-methylphenyl biphenyl ether, 1,2-bis(3,4-dimethylphenyl) ethane, 2,3,5,6-4'-methyldiphenyl methane, 1,4-diethoxynaphthalene, 1,4-diacetoxybenzene, 1,4-diproprionoxybenzene, o-xylylene-bis(phenyl ether), 4-(m-methylphenoxymethyl) biphenyl, p-hydroxyacetanilide, p-hydroxybutyranilide, p-hydroxynonananilide, p-hydroxylauranilide, p-hydroxyoctadecananilide, N-phenyl-phenylsulphonamide, acetyl biphenyl compounds (e.g. as described in JP2003 063149A2) and 2-phenoxyethyl-N-phenylcarbamate.

In a more preferred embodiment, the at least one sensitizer is selected from the group consisting of stearamide, amide waxes, benzyl-2-naphthyl ether, diphenyl sulfone, 1,2-diphenoxyethane and 1,2-bis(3-methylphenoxy) ethane.

In a preferred embodiment, the at least one stabilizer is selected from the group consisting of 2,2'-methylene-bis(4-methyl-6-tert-butylphenol), 2,2'-methylene-bis(4-ethyl-6-tert-butylphenol), 4,4'-butylidene-bis(3-methyl-6-tert-butylphenol), 4,4'-thio-bis(2-tert-butyl-5-methylphenol), 1,1,3-tris(2-methyl-4-hydroxy-5-tert-butylphenyl) butane, 1,1,3-tris(2-methyl-4-hydroxy-5-cyclohexylphenyl) butane; 1,1,3-Tris (3-cyclohexyl-4'-hydroxy-6-methylphenyl) butane, bis (3-tert-butyl-4-hydroxy-6-methylphenyl) sulfone, bis (3,5-dibromo-4-hydroxyphenyl) sulfone, 4,4'-sulfinyl bis (2-tert-butyl-5-methylphenol), 2,2'-methylene bis (4,6-di-tert-butylphenyl) phosphate and alkali metal, ammonium and polyvalent metal salts thereof, 4-benzyloxy-4'-(2-methylglycidyloxy) diphenyl sulfone, 4,4'-diglycidyloxydiphenyl sulfone, 1,4-diglycidyloxybenzene, 4-[α-(hydroxymethyl)benzyloxy]-4-hydroxydiphenyl sulfone, metal salts of p-nitrobenzoic acid, metal salts of phthalic acid mono benzyl ester, metal salts of cinnamic acid, 4,4'-sulfonyl bisphenol, polymer with 1,1'-oxybis[2-chloroethane] having CAS No. 191680-83-8, carbamic acid, N,N-[sulfonylbis[4,1-phenyleneiminocarbonylimino (methylphenylene]]bis-C,C-diphenyl ester (CAS No. 874187-71-0), 4,4'-sulfonylbis(benzeneamide) based compounds, reaction product of 4,4'-sulfonylbis(benzeneamine), 2,4-toluenediisocyanate and phenol (trade name UU).

In a more preferred embodiment, the at least one stabilizer is selected from the group consisting of 4,4'-butylidene-bis(3-methyl-6-tert-butylphenol), 4,4'-thio-bis(2-tert-butyl-5-methylphenol), 1,1,3-tris(2-methyl-4-hydroxy-5-tert-butylphenyl) butane, 1,1,3-tris(2-methyl-4-hydroxy-5-cyclohexylphenyl) butane, 4'-sulfonyl bisphenol polymer with 1,1'-oxybis[2-chloroethane] and carbamic acid, N,N-[sulfonylbis[4,1-phenyleneinninocarbonylinnino(methylphenylene]]bis-C,C-diphenyl ester.

In a preferred embodiment, the binder is at least one selected from the group consisting of poly-vinyl alcohol (fully or partially hydrolysed), carboxy-modified polyvinyl alcohol, acetoacetyl-modified polyvinyl alcohol, diacetone-modified polyvinyl alcohol, silicon-modified polyvinyl alcohol, sulfonic-modified polyvinyl alcohol, oxidised starch, gelatine, casein, derivatives of cellulose such as hydroxyethyl cellulose, methyl cellulose, ethyl cellulose, carboxymethyl cellulose and acetyl cellulose, starch-vinyl acetate graft copolymers, styrene-maleic anhydride copolymers, methyl vinyl ether-maleic anhydride copolymers, isopropylene-maleic anhydride copolymers, water-soluble resins, styrene-butadiene latex, acrylic latex, urethane latex and water-dispersible resins. In a preferred embodiment, the amount of the binder is 5 to 40 weight-%, preferably 7 to 30% by weight, based on dry weight of the heat sensitive recording layer.

In a preferred embodiment, the pigment is at least one selected from the group consisting of ground calcium carbonate, precipitated calcium carbonate, kaolin, calcined kaolin, aluminium hydroxide, talc, titanium dioxide, zinc oxide, amorphous silica, barium sulfate, polystyrene resin, urea-formaldehyde resin and hollow plastic pigment. The amount of the pigment is preferably in the range of 5 to 75 weight-%; more preferably 10 to 60 weight-% based on the dry weight of the heat sensitive recording layer.

In a preferred embodiment, the lubricant is at least one selected from the group consisting of stearamide, methylene bis stearamide, polyethylene wax, carnauba wax, paraffin wax, zinc stearate and calcium stearate. The amount of the lubricant is preferably in the range of 2 to 10 weight-%, more preferably of 3 to 7 weight-%, based on the dry weight of the heat sensitive recording layer.

In a preferred embodiment, the heat sensitive recording material composition comprises auxiliaries selected from surfactants such as sodium dioctyl sulfosuccinate, sodium dodecybenzene-sulfonate, sodium lauryl sulfate and fatty acid metal salts, insolubilisers such as glyoxal, urea-formaldehyde resins, melamine-formaldehyde resins, polyamide resins, polyamideamine-epichlorohydrin resins, adipic acid dihydrazide, boric acid, borax, ammonium zirconium carbonate and potassium zirconium carbonate, antifoaming agents, fluorescent whitening agents, fluorescent dyes and/or pigments, tinting dyes and UV absorbers. The amount of auxiliaries is preferably in the range of 0.1 to 5 weight-%, based on dry weight of the heat sensitive recording layer.

In a preferred embodiment, the heat sensitive recording material comprises ultraviolet absorbers. The ultraviolet absorbers are employed in either the heat sensitive recording material layer or in a protective layer. Optionally, the ultraviolet absorbers are used in microencapsulated form in the protective layer.

In a preferred embodiment, the ultraviolet absorbers are selected from the group consisting of salicylic acid derived ultraviolet absorbers, benzophenone derived ultraviolet absorbers, cyanoacrylate derived ultraviolet absorbers, hindered amine based ultraviolet absorbers, benzotriazole derived ultraviolet absorbers.

In a more preferred embodiment, the salicylic acid derived ultraviolet absorbers are selected from the group consisting of phenyl salicylate, p-tert-butylphenyl salicylate and p-octylphenyl salicylate.

In a more preferred embodiment, the benzophenone derived ultraviolet absorbers are selected from the group consisting of 2,4-dihydroxybenzophenone, 2-hydroxy-4-methoxybenzophenone, 2-hydroxy-4-octyloxybenzophenone, 2-hydroxy-4-dodecyloxybenzophenone, 2,2'-dihydroxy-4-methoxybenzophenone, 2,2'-dihydroxy-4,4'-dimethoxybenzophenone and 2-hydroxy-4-methoxy-5-sulfobenzophenone.

In a more preferred embodiment, the cyanoacrylate derived ultraviolet absorbers are selected from the group consisting of 2-ethylhexyl-2-cyano-3,3-diphenylacrylate and ethyl-2-cyano-3,3-diphenylacrylate.

In a more preferred embodiment, the hindered amine based ultraviolet absorbers are selected from the group consisting of bis(2,2,6,6-tetramethyl-4-piperidyl) sebacate, bis(2,2,6,6-tetramethyl-4-piperidyl) succinate and bis(1,2,2,6,6-pentamethyl-4-piperidyl)-2-(3,5-di-tert-butyl-4-hydroxybenzyl)-2-n-butyl malonate.

In a more preferred embodiment, the benzotriazole derived ultraviolet absorbers are selected from the group consisting of 2-(2'-hydroxyphenyl)benzotriazole, 2-(2'-hydroxy-5'-methylphenyl)benzotriazole, 2-(2'-hydroxy-5'-tert-butylphenyl)benzotriazole, 2-(2'-hydroxy-3',5'-di-tert-butylphenyl)benzotriazole, 2-(2'-hydroxy-3'-tert-butyl-5'-methylphenyl)-5-chlorobenzotriazole, 2-(2'-hydroxy-3',5'-di-tert-butylphenyl)-5-chlorobenzotriazole, 2-(2'-hydroxy-3,5'-di-tert-butylphenyl)-5-tert-butylbenzotriazole, 2-(2'-hydroxy-3,5'-di-tert-amylphenyl) benzotriazole, 2-(2'-hydroxy-3,5'-di-tert-amylphenyl)-5-tert-amylbenzotriazole, 2-(2'-hydroxy-3,5'-di-tert-amylphenyl)-5-methoxybenzotriazole, 2-[2'-hydroxy-3'-(3",4",5",6"-tetrahydrophthalinnidomethyl)-5'-methylphenyl] benzotriazole, 2-(2'-hydroxy-5'-tert-octylphenyl)benzotriazole, 2-(2'-hydroxy-3'-sec-butyl-5'-tert-butylphenyl) benzotriazole, 2-(2'-hydroxy-3'-tert-amyl-5'-phenoxyphenyl)-5-methylbenzotriazole, 2-(2'-hydroxy-5'-n-dodecylphenyl) benzotriazole, 2-(2'-hydroxy-5'-sec-octyloxyphenyl)-5-phenylbenzotriazole, 2-(2'-hydroxy-3'-tert-amyl-5'-phenylphenyl)-5-methoxybenzotriazole, 2-[2'-hydroxy-3',5'-bis($\alpha,\alpha$-dimethylbenzyl)-phenyl]benzotriazole, 2-(2'-Hydroxy-3'-dodecyl-5'-methylphenyl) benzotriazole, 2-(2'-hydroxy-3'-undecyl-5'-methylphenyl) benzotriazole, 2-(2'-hydroxy-3'-tridecyl-5'-methylphenyl) benzotriazole, 2-(2'-hydroxy-3'-tetradecyl-5'-methylphenyl) benzotriazole, 2-(2'-hydroxy-3'-pentadecyl-5'-methylphenyl) benzotriazole, 2-(2'-hydroxy-3'-hexaadecyl-5'-methylphenyl) benzotriazole, 2-[2'-hydroxy-4'-(2"-ethylhexyl)oxyphenyl] benzotriazole, 2-[2'-hydroxy-4'-(2"-ethylheptyl)oxyphenyl] benzotriazole, 2-[2'-hydroxy-4'-(2"-ethyloctyl)oxyphenyl] benzotriazole, 2-[2'-hydroxy-4'-(2"-propyloctyl)oxyphenyl] benzotriazole, 2-[2'-hydroxy-4'-(2"-propylheptyl)oxyphenyl] benzotriazole, 2-[2'-hydroxy-4'-(2"-propylhexyl)oxyphenyl] benzotriazole, 2-[2'-hydroxy-4'-(1"-ethylhexyl)oxyphenyl] benzotriazole, 2-[2'-hydroxy-4'-(1"-ethylheptyl)oxyphenyl] benzotriazole, 2-[2'-hydroxy-4'-(1"-ethyloctyl)oxyphenyl] benzotriazole, 2-[2'-hydroxy-4'-(1"-propyloctyl)oxyphenyl] benzotriazole, 2-[2'-hydroxy-4'-(1"-propylheptyl)oxyphenyl] benzotriazole, 2-[2'-hydroxy-4'-(1"-propylhexyl)oxyphenyl] benzotriazole, 2-(2'-hydroxy-3'-sec-butyl-5'-tert-butylphenyl)-5-n-butylbenzotriazole, 2-(2'-hydroxy-3'-sec-butyl-5'-tert-butylphenyl)-5'-tert-pentylbenzotriazole, 2-(2'-hydroxy-3'-sec-butyl-5'-tert-butylphenyl)-5-n-pentylbenzotriazole, 2-(2'-hydroxy-3'-sec-butyl-5'-tertpentylphenyl)-5'-tert-butylbenzotriazole, 2-(2'-hydroxy-3'-sec-butyl-5'-tert-pentylphenyl)-5'-n-butylbenzotriazole, 2-(2'-hydroxy-3',5'-di-tert-butylphenyl)-5-sec-butylbenzotriazole, 2-(2'-hydroxy-3',5'-di-tert-pentylphenyl)-5-sec-butylbenzotriazole, 2-(2'-hydroxy-3'-tert-butyl-5'-tert-pentylphenyl)-5-sec-butylbenzotriazole, 2-(2'-hydroxy-3,5'-di-sec-butylphenyl)-5-chlorobenzotriazole, 2-(2'-hydroxy-3,5'-di-sec-butylphenyl)-5-methoxybenzotriazole, 2-(2'-hydroxy-3,5'-di-sec-butylphenyl)-5-tert-butylbenzotriazole, 2-(2'-hydroxy-3,5'-di-sec-butylphenyl)-5-n-butylbenzotriazole, octyl-5-tert-butyl-3-(5-chloro-2H-benzotriazole-2-yl)-4-hydroxybenzene propionate and condensate of methyl-3-[tert-butyl-5-(2H-benzotriazole-2-yl)-4-hydroxyphenyl] propionate and polyethylene glycol (molecular weight: about 300).

In a preferred embodiment, the heat sensitive recording layer composition is applied to the support as a layer or coating in an amount in the range of 1 to 10 g/m²; more preferably 3 to 7 g/m² on a dry weight basis. The heat sensitive recording layer composition is applied to the support by a known coating device such as a coating bar, a roll coater, an air knife coater, a blade coater, a gravure coater, a die coater or a curtain coater.

Optionally, an undercoat layer is provided between the support and the heat sensitive recording layer in order to improve the thermal sensitivity and efficiency during recording.

The undercoat layer is provided by coating the support with an undercoat layer coating composition comprising as main components organic hollow particles and/or an oil absorbing pigment and a binder, and then drying the coating.

In a preferred embodiment, the oil absorbing pigment is selected from the group consisting of kaolin, calcined kaolin, amorphous silica, precipitated calcium carbonate and talc. The average oil absorbing pigment diameter is in the range of 0.01 to 5 μm, preferably of 0.02 to 3 μm.

In a preferred embodiment, the organic hollow particles are selected from the group consisting of particles having a shell made from an acrylic resin, styrene-based resin and vinylidene chloride-based resin and having a void ratio in the range of 50 to 99%. The outside diameter of the organic hollow particle is preferably in the range of 0.5 to 10 μm, more preferably of 1 to 5 μm.

In a preferred embodiment, the organic hollow particles are expandable hollow particles such as microcapsules having an average diameter of 0.1 to 5 μm and comprising a vinylidene chloride resin shell and butane gas as fill material. When a support coated with an undercoat layer comprising such expandable hollow particles is subjected to heat treatment, the microcapsules expand to an average particle diameter in the range of 1 to 30 μm.

In a preferred embodiment, the undercoat layer comprises the oil absorbing pigment and the organic hollow particles. The combined amount of the two components is preferably in the range of 40 to 90 weight-%, more preferably 50 to 80 weight-% based on the total weight of the undercoat layer.

In a preferred embodiment, the undercoat layer comprises a binder used in the heat sensitive recording layer; more preferably styrene-butadiene latex, a polyvinyl alcohol or starch-vinyl acetate copolymer. The amount of binder is preferably in the range of 5 to 30 weight-%, particularly 10 to 20 weight-%, based on the total weight of the undercoat layer.

In a preferred embodiment, the undercoat layer coating composition is applied to the support in an amount in the range of 2 to 20 g/m²; more preferably 4 to 12 g/m² on a dry weight basis.

Optionally, a protective layer is provided on the heat sensitive recording material layer to enhance the resistance of the recorded image to water and chemicals such as oils, fats, alcohols, plasticisers and the like as well as to improve the runability during recording.

In a preferred embodiment, the protective layer is formed by coating the heat sensitive recording layer with a protective layer coating composition comprising as main components a binder having film-forming ability and optional components selected from the group consisting of pigment, insolubiliser and lubricant, and then drying to obtain the protective layer coating film.

In a preferred embodiment, the binder used in the protective layer coating composition is at least one selected from the group consisting of polyvinyl alcohol (fully or partially hydrolysed), carboxy-modified polyvinyl alcohol, acetoacetyl-modified polyvinyl alcohol, diacetone-modified polyvinyl alcohol, silicon-modified polyvinyl alcohol, starches, gelatine, casein, gum arabic, derivatives of cellulose such as hydroxyethyl cellulose, methyl cellulose, ethyl cellulose, carboxymethyl cellulose and acetyl cellulose, starch vinyl acetate graft copolymers, styrene-maleic anhydride copolymers, methyl vinyl ether-maleic anhydride copolymers, isopropylene-maleic anhydride copolymers, water-soluble resins, styrene-butadiene latex, acrylic latex, urethane latex and water-dispersible resins.

In a preferred embodiment, the optional auxiliaries such as pigment, insolubiliser, and lubricant used in the protective layer coating composition are selected from those used in the heat sensitive recording material layer coating composition as described above.

It is also possible to provide a protective layer, an adhesive layer and a magnetic layer on the rear side of the support.

Embodiments

In the following, there is provided a list of embodiments to further illustrate the present disclosure without intending to limit the disclosure to the specific embodiments listed below.

1. A compound of formula (1)

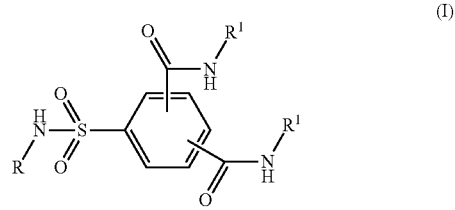

(I)

wherein

R and $R^1$ are independently selected from the group consisting of hydrogen, linear or branched $C_1$-$C_{18}$-alkyl, $R^{11}O$—$R^{12}$— wherein $R^{11}$ and $R^{12}$ are independently linear or branched $C_1$-$C_8$-alkyl, $(R^{13})_2N$—$R^{12}$— wherein $R^{13}$ is a linear or branched $C_1$-$C_8$-alkyl or together with the nitrogen to which they are attached form a 5 or 6 membered ring, and $R^{12}$ is as defined earlier, and a radical of formula (II)

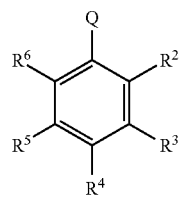

wherein, $R^2$, $R^3$, $R^4$, $R^5$, and $R^6$ are independently selected from the group consisting of
hydrogen,
linear or branched $C_1$-$C_8$-alkyl,
—NH—C(=O)—$R^{14}$, —C(=O)—NH—$R^{14}$, wherein $R^{14}$ is linear or branched $C_1$-$C_8$-alkyl,
—C(=O)O$R^{15}$, wherein $R^{15}$ is linear or branched $C_1$-$C_8$-alkyl, and
halogen, or
$R^2$ and $R^3$, or $R^4$ and $R^5$ or both, or
$R^3$ and $R^4$, or $R^5$ and $R^6$ or both, or
$R^2$ and $R^3$ as well as $R^5$ and $R^6$ together form a hydrocarbon diradical comprising 3 or 4 carbon atoms;
and
Q is a single bond or branched or unbranched $C_1$-$C_8$-alkylene, optionally comprising one or more oxygen atoms.

2. The compound according to embodiment 1,

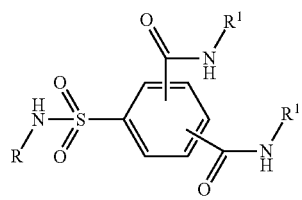

wherein
R and $R^1$ are independently selected from the group consisting of
hydrogen,
linear or branched $C_1$-$C_{18}$-alkyl, and
a radical of formula (II)

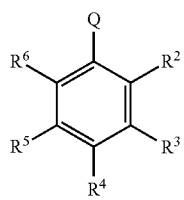

wherein, $R^2$, $R^3$, $R^4$, $R^5$, and $R^6$ are independently selected from the group consisting of
hydrogen, and
linear or branched $C_1$-$C_8$-alkyl, and
Q is a single bond.

3. The compound according to embodiment 1 or 2 is compound of formula (III)

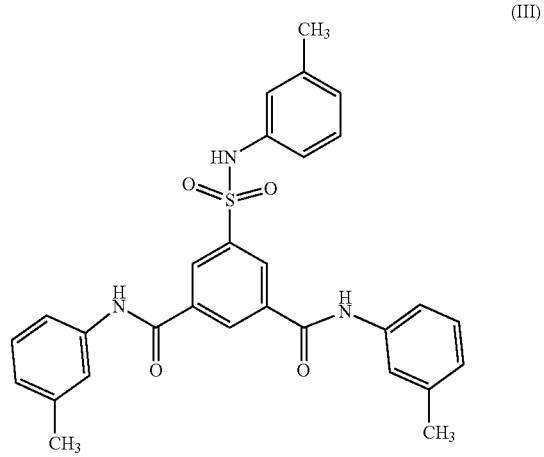 [SMILES: Cc1cccc(NC(=O)c2cc(C(=O)Nc3cccc(C)c3)cc(S(=O)(=O)Nc3cccc(C)c3)c2)c1]

4. The compound according to embodiment 3, wherein the compound is a crystalline polymorph form a that is characterized by an X-ray powder diffraction pattern comprising 2Θ reflections, plus or minus 0.2 degrees 2Θ, at 5.5, 6.1, 6.4, 12.1, 16.1, 16.8, 17.1, 18.3, 19.1, 19.9, 20.2, 21.4, 22.1, 22.7, 23.3, 24.3, 24.7, 25.0, 26.4, 27.7 and 29.3.

5. The compound according to embodiment 3, wherein the compound is a crystalline polymorph form β that is characterized by an X-ray powder diffraction pattern comprising 2Θ reflections, plus or minus 0.2 degrees 2Θ, at 6.2, 8.1, 10.1, 11.8, 12.2,13.4, 14.1, 15.3, 16.1, 17.2,18.4, 19.1, 20.6, 21.4, 22.4, 24.5, 25.0, 25.9, 26.2, 26.9 and 28.4.

6. A process for preparing a compound of formula (I) comprising the following steps,
   a. chlorinating a sulfo-isophthalic compound (IVa) with a chlorination agent to obtain an acid chloride of formula (IVb),

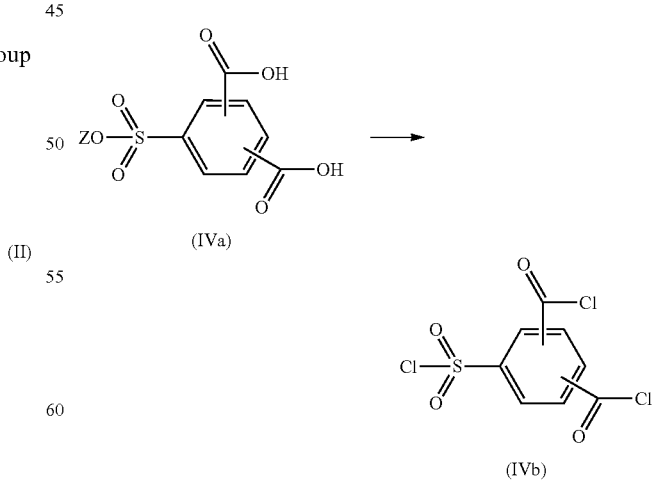

wherein Z stands for hydrogen or an alkali metal;
   b. optionally, isolating the acid chloride (IVb);
   c. reacting the acid chloride (IVb) with at least one amine to obtain the compound of formula (I).

7. The process according to embodiment 6 or 7, wherein the chlorination agent is selected from the group consisting of thionyl chloride, POCl₃, PCl₅ and oxalyl chloride.
8. The process according to embodiment 6 or 7, wherein acid chloride (IVb) is 5-sulfonylchloride-isophthalic acid dichloride.
9. The process according to any of embodiments 6 to 8, wherein the at least one amine is selected from the group consisting of ammonia, linear or branched $C_1$-$C_{18}$-alkylamine, $R^{11}O$—$R^{12}$—$NH_2$, wherein $R^{11}$ and $R^{12}$ are independently linear or branched $C_1$-$C_8$-alkyl, $(R^{13})_2N$—$R^{12}$—$NH_2$, wherein $R^{13}$ is a linear or branched $C_1$-$C_8$-alkyl or together with the nitrogen to which they are attached form a 5 or 6 membered ring, and $R^{12}$ is as defined earlier, and an amine of formula (IIa)

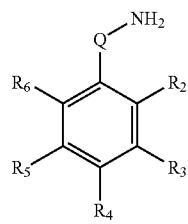

(IIa)

wherein, $R^2$, $R^3$, $R^4$, $R^5$, and $R^6$ are independently selected from the group consisting of hydrogen, linear or branched $C_1$-$C_8$-alkyl, —NH—C(=O)—$R^{14}$, —C(=O)—NH—$R^{14}$, wherein $R^{14}$ is linear or branched $C_1$-$C_8$-alkyl, —C(=O)O$R^{15}$, wherein $R^{15}$ is linear or branched $C_1$-$C_8$-alkyl, and halogen, or $R^2$ and $R^3$, or $R^4$ and $R^5$ or both, or $R^3$ and $R^4$, or $R^5$ and $R^6$ or both, or $R^2$ and $R^3$ as well as $R^5$ and $R^6$ together form a hydrocarbon diradical comprising 3 or 4 carbon atoms;

and

Q is a single bond or branched or unbranched $C_1$-$C_8$-alkylene, optionally comprising one or more oxygen atoms.

10. The process according to any of embodiments 6 to 9, wherein step c. comprises reacting the acid chloride of formula (IVb) with an amine $RNH_2$ to obtain compound of formula (I), wherein $R^1$ is identical to R.
11. The process according to any of embodiments 6 to 10, wherein the amine is m-toluidine.
12. The process according to any of embodiments 6 to 9, wherein step c. comprises the following sub-steps,
   i. reacting an acid chloride of formula (IVb) with a first amine $R^1NH_2$ to obtain compound of formula (V),

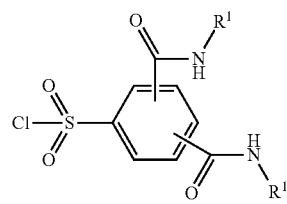

(V)

ii. reacting the product obtained in substep i. with a second amine $RNH_2$ to obtain compound of formula (I) wherein R and $R^1$ are different.
13. Use of a compound of formula (I) as a color developer in a heat sensitive recording material.
14. A heat sensitive recording material comprising
   A) at least one color former, and
   B) at least one color developer of formula (I)

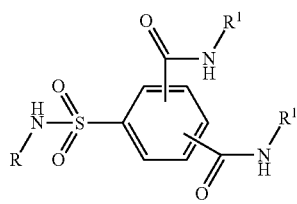

(I)

wherein R and $R^1$ are defined as in any of embodiments 1 to 5.

15. The heat sensitive recording material according to embodiment 14, wherein the weight ratio of color developer to color former is in the range of 1.5:1 to 3:1.
16. The heat sensitive recording material according to embodiment 14 or 15 further comprising at least one sensitizer.
17. The heat sensitive recording material according to embodiment 16, wherein the weight ratio of color developer to sensitizer is in the range of 0.5:1 to 1.5:1.
18. The heat sensitive recording material according to any of embodiments 14 to 17 further comprising at least one stabilizer.

Having generally described the invention, a further understanding can be obtained by reference to certain specific examples which are provided herein for the purpose of illustration only, and are not intended to be limiting unless otherwise specified.

EXAMPLES

The presently claimed invention is further illustrated in combination with the following examples. These examples are provided to exemplify the presently claimed invention, but are not intended to restrict the scope of the presently claimed invention in any way.

Materials

TAMOL® NN 9401 sodium salt of naphthalene sulfonic acid condensation product with formaldehyde, Pergascript Black 2C 3-dibutylamino-6-methyl-7-anilno-fluoran, Pergaspeed 305 benzyl-2-naphthyl ether, DISPEX® AA 4140 sodium polyacrylate, DISPEX® N40 sodium polyacrylate, Ansilex® 93 calcined kaolin, All materials available from BASF SE, Ludwigshafen/ Rhine, Germany.

Mowiol 40-88 10% by weight solution of polyvinyl alcohol Mw~205.000 g/mol is available from Sigma-Aldrich Inc./ Kuraray Europe GmbH.

Mowiol® 4-88 10% aqueous solution of polyvinyl alcohol MW 31.000 is available from Sigma-Aldrich Inc.

Gohsenx™ L-3266 10% aqueous solution of sulfonated polyvinyl alcohol is available from Nippon Gohsei.

Surfynol® 131 surfactant 2,4,7,9-tetramethyl-5-decyne-4,7-diol is available from Evonik.

Martinal OL-107 Aluminium trihydroxide is available from Martinswerk GmbH, Germany.

Sipernat® 350 amorphous silica is available from EVONIK Resource Efficiency GmbH, Germany.

SOCAL P3 precipitated calcium carbonate is available from Imerys GmbH.

Lowinox CA22 (=Topanol CA) 1,1,3-Tris(2'-methyl-4'-hydroxy-5'-t-butylphenyl)butane is available from Addivant.

Hidorin® F115 zinc stearate is available from Chukyo Europe.

UU reaction product of 4,4'-sulfonylbis(benzeneamine), 2,4-toluenediisocyanate and phenol is available from Asahi Kasei Corp.

Surfynol 104 PG 50 (50% solution of 2,4,7,9-tetramethyl-5-decyne-4,7-diol in propylene glycol) is available from Evonik Resource Efficiency GmbH, Germany.

I) Synthesis of 5-Sulfonylchloride-Isophthalic Acid Dichloride

Example 1

Synthesis of 5-Sulfonylchloride-Isophthalic Acid Dichloride

To a mixture of 42 g (150 mmol) of 5-sulfo-isophthalic acid sodium salt (95%) and 160 ml (2200 mmol) thionyl chloride (>99% GC) was added 10 ml of N, N-dimethylformamide under stirring to obtain a suspension. The suspension was slowly heated to reflux temperature followed by heating under reflux for two hours. The progress of the reaction was monitored by the formation of HCl and $SO_2$.

After the formation of gases ceased, the reaction mixture was cooled to room temperature. The yellowish suspension obtained was poured slowly over 1000 g of ice flakes with continuous stirring during which a slightly pinkish product precipitated. After stirring for additional 30 min at a temperature below 5° C. the precipitate was filtered to obtain a filter cake. The wet filter cake was stored in deep frozen and freeze-dried in order to avoid premature hydrolysis.

Yield: 45.5 g slightly yellowish powder
$^1$H-NMR ($d_6$-DMSO, δ): 9.15 (1H), 9.04 (2H)

II) Synthesis of Symmetrically Substituted Products ($R=R_1$)

Synthesis of 5-(N-Benzyl-sulfonylamido)-(N',N''-dibenzyl)-isophthalic acid-diamide was carried out by three methods depending upon the solvent used. The solvent used in Method A, Method B and Method C was water, t-butyl-methyl ether and toluene respectively.

(Method A)

Example 2

5-(N-Benzyl-Sulfonylamido)-(N',N''-Dibenzyl)-Isophthalic Acid-Diamide (Water)

15 g (50 mmol) 5-sulfonylchloride-isophthalic acid dichloride (synthesized according to example 1) was suspended in 125 ml of demineralized water (which was cooled and maintained at a temperature in the range of 0 to 5° C.). 32.7 g (310 mmol) Benzylamine (≥99%, Sigma-Aldrich Inc.) was slowly added to the suspension over a period of 20 minutes under continuous stirring at a temperature in the range of 0 to 5° C. After the addition of benzylamine was over a suspension containing white solid was formed; the suspension was further stirred for 22 hours. Water (100 ml) was added to the suspension, the precipitate obtained was filtered. The filtered precipitate was washed with 500 ml water and subsequently with 150 ml of hydrochloric acid (10%) to obtain a filter cake. The filter cake was dried under reduced pressure (200 mbar) at 50° C.

Yield: 20.5 g (86%) as white powder
melting point: 190° C.

(Method B)

Example 3

5-(N-Benzyl-Sulfonylamido)-(N',N''-Dibenzyl)-Isophthalic Acid-Diamide (t-Butyl-Methylether)

3 g (10 mmol) 5-Sulfonylchloride-isophthalic acid dichloride (synthesized according to example 1) was dissolved in 15 ml t-butyl-methyl ether. The clear solution was stirred for 15 min at room temperature and then cooled down to a temperature in the range of 0 to 5° C. A solution of 4.37 g benzylamine (≥99%, Sigma-Aldrich Inc.) in t-butyl-methyl ether was added to the cooled solution over a period of 60 min under stirring. A white precipitate was formed; the reaction mixture was further stirred for 1 h at a temperature in the range of 0 to 5° C., and later the temperature was increased to room temperature. The precipitate was filtered off and the filtered precipitate was washed subsequently with 30 ml t-butyl methyl ether, 50 ml water and 30 ml HCl (10%) to obtain white product. The white product was dried under a reduced pressure (200 mbar/50° C.) overnight.

Yield: 4.18 g (82%) as white powder.

Example 3a 5-(N-Benzyl-Sulfonylamido)-(N',N''-Dibenzyl)-Isophthalic Acid-Diamide 25 g (0.088 mol) of 5-Sulfonylchloride-isophthalic acid dichloride was dissolved in 500 ml toluene. Under stirring, 53.5 g (0.499 mol) benzylamine was added dropwise to the solution over a period of 30 minutes. After complete addition, the reaction mixture was additionally stirred for one hour at 25° C. The formed precipitate was collected by filtration to obtain a wet cake. The wet cake was washed with 200 ml of toluene to obtain a residue. The residue was extracted with 500 ml of ethyl acetate. The ethyl acetate layer was washed with 300 ml of water and then evaporated to dryness under reduced pressure at 60° C. to obtain the product.

Yield: 38 g, white crystals (89%),

¹H-NMR (d₆-DMSO, δ): 4.1 (2H), 4.5 (4H), 5.2 (2H), 7.1 7.5 (15H), 8.4 (2H) and 8.6 (1H), 9. (1H) ppm.
MS: m/z 512 (M−1)⁺, m.p. 166° C. (determined by DSC). (Method C)

Example 4

5-(N-3-Methylphenyl-Sulfonylamido)-(N',N''-bis-(3-Methylphenyl)-Isophthalic Acid-Diamide (Toluene)

1.5 g (5 mmol) 5-Sulfonylchloride-isophthalic acid dichloride (synthesized according to example 1) was dispersed in 20 ml toluene at room temperature. 3.3 g (30.9 mmol) 3-Methyl-aniline was slowly added to the white dispersion. A further 60 ml toluene was added to the crude suspension and the suspension was then heated at 100° C. for 18 h. After cooling to room temperature, the precipitate was filtered. The filtered precipitate was washed with 30 ml toluene, followed by 50 ml demineralized water and 30 ml HCl (10%). The compound thus obtained was dried under reduced pressure (200 mbar) at 40° C. to obtain the product.
Yield: 2 g of a reddish product
Recrystallization
10 g crude 5-(N-3-methylphenyl-sulfonylamido)-(N',N''-bis-(3-methylphenyl)-isophthalic acid-diamide obtained according to example 4 was dissolved in 350 ml methanol under reflux conditions to obtain in a clear solution. 35 ml Water was slowly added to the clear solution while heating under reflux conditions. After complete addition of water, a slightly hazy solution was obtained. The mixture was slowly cooled to room temperature over a period of 2 h. A white precipitate was obtained in the form of needles which was isolated by filtration. The white precipitate was washed with 50 ml of demineralized water and dried at 50° C. under reduced pressure (200 mbar).
Yield: 52%.
Melting point (DSC, 4° C/min): 195.3° C., 215.2° C.
An X-ray powder pattern of this material is having Bragg angles (2θ/CuK$_α$) of 8.1±0.2, 10.1±0.2, 11.9±0.2, 12.3±0.2, 13.4±0.2, 14.1±0.2 15.3±0.2, 16.1±0.2, 17.3±0.2, 18.4±0.2, 19.2±0.2, 20.6, ±0.2, 21.4±0.2, 22.4±0.2, 24.6±0.2, 25.1±0.2, 25.9±0.2, 26.3±0.2, 26.9±0.2 and 28.4±0.2.
¹H-NMR (d₆-DMSO, δ): 2.20 (3H), 2.32 (6H), 6.85 (1H), 6.92 (1H), 6.96 (3H), 7.11 (1H), 7.26 (2H), 7.58 (4H), 8.46 (2H), 8.73 (1H), 10.45 (1H), 10.53 (2H).
(Method D)

Example 5

5-(N-2,6-Diethylphenyl-Sulfonylamido)-(N',N''-bis-(2,6-Diethylphenyl)-Isophthalic Acid-Diamide (Ethanol)

To a mixture of 1.5 g (5 mmol) 5-sulfonylchloride-isophthalic acid dichloride (synthesized according to example 1) and 25 ml ethanol cooled down to a temperature in the range of 0 to 5° C., 2.4 g (16.1 mmol) 2,6-diethyl-aniline was added slowly under stirring. After stirring for 1 h at a temperature in the range of 0 to 4° C., the yellow-grey suspension was heated to the boiling point under reflux and maintained under reflux for 30 minutes during which the color changed to beige-red. The reaction mixture was then cooled to 10° C., the precipitate was isolated by filtration and washed with 20 ml of ethanol.
Yield: 0.3 g of colorless needles
From the filtrates, a further 1 g of colorless needles could be isolated by evaporation of the solvent.
Combined yield: 1.3 g (41%) 5-(N-2,6-diethylphenyl-sulfonylamido)-(N',N''-bis-(2,6-diethylphenyl)-isophthalic acid-diamide
Melting point: >210° C.

III) Crystal Modifications of 5-(N-3-Methylphenyl-Sulfonylamido)-(N',N''-Bis-(3-Methylphenyl)-Isophthalic Acid-Diamide

Example 4a

α-Modification

Directed synthesis of the α-modification of 5-(N-3-methylphenyl-sulfonylamido)-(N',N''-bis-(3-methylphenyl)-isophthalic acid-diamide
To a mixture of 49.0 g (0.16 mol) of 5-sulfonylchloride-isophthalic acid dichloride (synthesized according to example 1) and 500 ml of toluene at 22° C., 110 ml (0.99 mol) m-toluidine was added dropwise over a period of 30 minutes. Additional 500 ml toluene was added and the reaction mixture obtained was heated to 100° C. Additional 1500 ml of toluene was added, and the reaction mixture was heated at 100° C. for 3 hours. The reaction mixture was then allowed to cool to 22° C. The precipitate formed was filtered off.
The filter cake obtained was suspended in 250 ml of water under stirring. This suspension was heated at 80° C. for 30 min. The aqueous layer was removed by decantation at 80° C. Then 200 ml of 10% by weight hydrochloric acid was added to the residue and the mixture was stirred for 30 min at 40° C. Then, the aqueous layer was decanted. n-Heptane (800 ml) was added to the residue and stirred for 30 minutes at 22° C. The precipitate was collected by filtration and dried under the reduced pressure of a vacuum pump at 60° C.
Yield: 81 g (96%), white solid, m.p. 211.2° C. (DSC), bulk density 240 kg/m³.
An X-ray powder pattern of this material is having Bragg angles (2θ/CuK$_α$) of 5.5±0.2, 6.1±0.2, 6.4±0.2, 12.1±0.2, 16.1±0.2, 16.8±0.2, 17.1±0.2, 18.3±0.2, 19.1±0.2, 19.9±0.2, 20.2±0.2, 21.4±0.2, 22.1±0.2, 22.7±0.2, 23.3±0.2, 24.3±0.2, 24.7±0.2, 25.0±0.2, 26.4±0.2, 27.7±0.2 and 29.3±0.2.

Example 4b

β-Modification

Directed synthesis of the β-modification of 5-(N-3-methylphenyl-sulfonylamido)-(N',N''-bis-(3-methylphenyl)-isophthalic acid-diamide
To a mixture of 10.8 g (0.1 mol) of m-toluidine in 50 ml tetrahydrofuran at 22° C., a solution of 5.0 g (0.0166 mol) 5-sulfonylchloride-isophthalic acid dichloride (synthesized according to example 1) in 15 m tetrahydrofuran was added dropwise over a period of 15 min under stirring. The reaction mixture was heated to 65° C. for 5 hours. The formed precipitate was isolated by filtration. The filtrate was dried under reduced pressure. The obtained residue was mixed with 25 ml tetrahydrofuran. The solution obtained was poured into 100 ml of a methanol/water (9:1) mixture and heated to 50° C. for one hour. The heated mixture was then cooled down to 22° C. The solid obtained was collected by filtration and washed with methanol. The product was then dried under reduced pressure at 60° C. for 7 hours.
Yield: 5.0 g (58%), white solid, m.p. 192.2° C. (DSC)
An X-ray powder pattern of this material is having Bragg angles (2θ/CuK$_α$) of 6.2±0.2, 8.1±0.2, 10.1±0.2, 11.8±0.2, 12.2±0.2, 13.4, ±0.2 14.1±0.2, 15.3±0.2, 16.1±0.2, 17.2±0.2, 18.4±0.2, 19.1±0.2, 20.6±0.2, 21.4±0.2, 22.4±0.2, 24.5±0.2, 25.0±0.2, 25.9±0.2, 26.2±0.2, 26.9±0.2 and 28.4. ±0.2.

Example 4c

γ-Modification

Directed synthesis of the γ-modification of 5-(N-3-methylphenyl-sulfonylamido)-(N',N''-bis-(3-methylphenyl)-isophthalic acid-diamide To a mixture of 10.8 g (0.1 mol) m-toluidine and 75 ml n-heptane, 5 g (0.0166 mol) 5-sulfonylchloride-isophthalic acid dichloride (synthesized according to example 1) in 20 ml toluene was added dropwise over a period of 45 minutes at 75° C. The reaction mixture was heated to 90° C. and stirred at this temperature for 5 hours, and then cooled to 60° C. Subsequently, 50 ml of water, followed by 5 ml of concentrated hydrochloric acid were added at this temperature to the reaction mixture, and then stirred for another 15 minutes at 60° C. The solid phase obtained was collected by filtration at this temperature. The filter cake obtained was washed first with 50 ml of water, then with 50 ml of n-heptane and subsequently dried on a suction filter for 1 hour.

The dried filter cake was suspended in 90 ml of a methanol/water mixture (9:1) and the suspension was stirred for two hours at 60° C. After cooling the suspension to 20° C., the precipitate was filtered off and washed with 50 ml of a methanol/water mixture (1:1). The product was dried under the reduced pressure at 60° C. for 7 hours.

Yield: 7.0 g (white solid) 82%, m.p. 215.6° C., determined by DSC.

An X-ray powder pattern of this material is having Bragg angles (2θ/CuK$_α$) of 5.5±0.2, 6.1±0.2, 6.4±0.2, 9.6±0.2, 12.2±0.2, 12.7±0.2, 16.1±0.2, 16.8±0.2, 17.1±0.2, 18.2±0.2, 19.2±0.2, 20.5±0.2, 22.7±0.2, 23.3±0.2, 24.8±0.2, 26.4±0.2, 27.6±0.2, 29.2±0.2, 30.4±0.2, 32.0±0.2, 35.7±0.2 and 38.8±0.2.

IV) One Step Procedure

Example 4d

One step procedure for the synthesis of 5-(N-3-methylphenyl-sulfonyl-amido)-(N',N''-bis-(3-methylphenyl)-isophthalic acid diamide
  a) Synthesis of 5-sulfonylchloride-isophthalic acid dichloride A suspension of 150 ml (2.1 mol) thionyl chloride and 125 g (0.47 mol) 5-sulfo isophthalic acid sodium salt was heated to 70° C. At this temperature, a solution of 3.4 g (0.05 mol) N,N-dimethylformamide in 100 ml thionyl chloride is added via a dropping funnel over a period of 1.5 hours. The reaction mixture was stirred for 2.5 hours at 70 -75° C. until the gas evolution stopped. The formation of crude acid chloride was monitored by LC. After complete reaction, the excess of thionyl chloride was removed by distillation. The acid chloride was obtained as jelly mass along with fine sodium chloride crystals. The mass was filtered and the filtrate was collected. 350 ml of toluene are added to the filtrate to obtain 450-500 g of a solution of 5-sulfonylchloride isophthalic acid dichloride.
  b) Conversion of 5-sulfonylchloride-isophthalic acid dichloride to corresponding acid acid trisamide A solution of 3 g Surfynol 104 PG 50 (50% solution in propylene glycol, Evonik) and 27 g (0.33 mol) sodium bicarbonate in 300 ml water was stirred at 20° C. 35 g (0.33 mol) of m-toluidine was added in one portion. The solution was heated to 30-40° C. A solution of 100 g (~0.1 mol) intermediate solution prepared in step 1 is added over a period of 1.5 hours. The formed reaction suspension was heated-up to 50-55° C. and kept at this temperature under stirring for 2 hours. The reaction was monitored by LC. When the conversion was complete, the reaction mixture was cooled to 20° C. The formed precipitate was collected by the filtration at a suction filter. The obtained crude wet cake was washed with around 210 ml of water, then with 210 ml of toluene and afterwards dried for 12 hours under vacuum at 50° C.

Yield: 45 g (86%), white solid, bulk density 550 kg/m³.

An X-ray powder pattern of this material is having Bragg angles (2θ/CuK$_α$) of 5.4±0.2, 6.1±0.2, 6.3±0.2, 11.9±0.2, 12.6±0.2, 15.9±0.2, 16.6±0.2, 16.9±0.2, 18.1±0.2, 19.1±0.2, 19.7±0.2, 20.3±0.2, 22.0±0.2, 22.5±0.2, 23.1±0.2, 24.1±0.2, 24.9±0.2, 25.4±0.2, 26.3±0.2, 27.7±0.2 and 29.1±0.2.

Symmetrically substituted compounds 6-14 listed in Table 1 were prepared using the procedure mentioned above.

TABLE 1

Symmetrically substituted compounds 6-14 prepared according to methods A, B and C

| Examples | Substituent R=R$_1$ | Method | Mp (° C.) | Yield (%) |
|---|---|---|---|---|
| 6 | phenyl | C | 187->200 | 85 |
| 7 | o-i-propyl-phenyl- | C | >200 | 42 |
| 8 | p-acetamido-phenyl- | C | >200 | 90 |
| 9 | 1-tetralino- | B | 134-140 | 98 |
| 10 | 1-phenylethyl- | B | 120-123 | 79 |
| 11 | 2-phenylethyl- | B | 140-141 | 85 |
| 12 | 2,6-diethylphenyl- | C | >210 | 66 |
| 13 | butyl- | A | 120 | 64 |
| 14 | 2-ethyl-hexyl- | A | nm* | 57 |

*nm: not measured

Example 10a 5-(N-1-Phenylethyl-Sulfonylamido)-(N',N''-bis-(1-Phenylethyl)-Isophthalic Acid-Diamide 25 g (0.088 mol) of 5-sulfonylchloride-isophthalic acid dichloride was dissolved in 200 ml toluene. Under stirring, 60 g (0.495 mol) racemic 1-phenyl ethylamine and 100 ml of toluene was added dropwise over a period of 40 minutes. The reaction mixture was heated at 75° C. for one hour. The formed precipitate was collected by filtration in a suction filter. The wet cake was washed with 200 ml of toluene. The residue was suspended in 300 ml of ethyl acetate and heated to 75° C. The obtained slurry was filtered. The filtrate was washed with 200 ml of water and then evaporated to dryness under reduced pressure at 60° C.

Yield: 50 g, white crystals (76%), m.p. 182° C. (determination by DSC)

$^1$H-NMR (d$_6$-DMSO, δ): 1.3 (3H), 1.6(6H), 4.5 (1H), 5.2 (2H), 6.8-7.4 (15H), 8.1 (2H) and 8.2 ppm.

MS=m/z 555.9 (M)$^+$.

The compound described in example 12 was prepared according the following procedure:

Example 12a 5-(N-2,6-Diethylphenyl-Sulfonylamido)-(N',N''-bis-(2,6-Diethylphenyl)-Isophthalic Acid-Diamide 25 g (0.088 mol) of 5-sulfonylchloride-isophthalic acid dichloride was dissolved in 500 ml toluene. Under stirring, 66.7 g (0.45 mol) 2,6-diethylaniline and 100 ml of toluene was added dropwise over a period of 30 minutes. During the addition, the temperature increased to 40° C. The reaction mixture was kept under stirring at 40° C. for three hours. The formed precipitate was collected by filtration in a suction filter. The wet cake was subsequently washed with 200 ml of toluene, and twice with 100 ml of demineralized water and then dried under reduced pressure at 60° C.

Yield: 48 g, white crystals (94%), m.p. 122° C. (determination by DSC),

MS=m/z 639.1 (M)$^+$.

$^1$H-NMR (d$_6$-DMSO, δ): 1.1-1.2 (aliphatic H), 2,5-2.6 (aliphatic H), 7.1-7.3 (Aryl-H), 8.4 and 8.6 (Aryl-H), 10.1 (NH) ppm.

V) Synthesis of Asymmetrically Substituted Products (R≠R$_1$)

(Method F)

Example 15

5-(N-Benzyl-Sulfonylamido)-(N',N''-Diphenyl-Isophthalic Acid-Diamide (Toluene)

To a mixture of 1.5 g (5 mmol) 5-sulfonylchloride-isophthalic acid dichloride (synthesized according to example 1) and 25 ml toluene at 80° C., 1.06 g (11 mmol) of aniline was slowly added. After stirring at a temperature in the range of 85 to 90° C. for 5 hours, a suspension was obtained, which was cooled to room temperature. 1.7 g (15.9 mmol) benzylamine was added and the reaction mixture was stirred for a further 17 h at a temperature in the range of 60 to 65° C. After cooling to room temperature, the precipitate obtained was filtered and subsequently washed with 30 ml toluene, followed by 50 ml demineralized water and 30 ml of HCl (10%). The wet filter cake was dried under reduced pressure (200 mbar) at 40° C.

Yield: 1.7 g (70%) white powder of 5-(N-benzyl-sulfonylamido)-(N',N''-bisphenyl-isophthalic acid-diamide The following asymmetrically substituted products were obtained by the procedure mentioned herein above:

Compounds 16-25 listed in Table 2 were prepared using the procedure mentioned above.

TABLE 2

Asymmetrically substituted compounds prepared according to method F

| Examples | R | R$_1$ | Yield (%) |
|---|---|---|---|
| 16 | phenyl- | benzyl- | 56 |
| 17 | benzyl- | 3-methyl-phenyl- | 71 |
| 18 | butyl- | 3-methyl-phenyl- | 82 |
| 19 | 1-phenyl-ethyl- | 3-methyl-phenyl- | 72 |
| 20 | 2-phenyl-ethyl- | 3-methyl-phenyl- | 79 |
| 21 | 2-methoxy-ethyl- | 3-methyl-phenyl- | 96 |
| 22 | octyl- | 3-methyl-phenyl- | 95 |
| 23 | benzyl- | 2,6-diethylphenyl- | 100 |
| 24 | octyl- | 2,6-diethylphenyl- | 64 |
| 25 | 2-phenoxy-ethyl- | 2,6-diethylphenyl- | 88 |

VI) Application Examples: Preparation of Compositions

The following non-limiting examples illustrate the application of the compounds of the present application as a color developer.

Milling Example 1:

Preparation of color developer dispersion

Comparative examples A-1 to A-4

The properties of the compounds of the present application were compared with the existing color developers. For this purpose color developer dispersions A-1 to A-4 were prepared.

Preparation of Color Developer Dispersion A-1

A mixture of 5 g of N-p-toluenesulfonyl-N'-3-(p-toluenesulfonyloxy)phenylurea (Pergafast 201, BASF SE), 0.1 g of a dispersing agent (sodium salt of naphthalene sulfonic acid condensation product with formaldehyde, TAMOL® NN 9401 from BASF SE), 3.4 g of a 10% by weight solution of polyvinyl alcohol (Mowiol® 40-88, Mw~205.000 g/mol, Sigma-Aldrich Inc./Kuraray Europe GmbH) and 11.5 g of water was milled in a bead mill to an average particle diameter of 1.0 μm to obtain Dispersion A-1.

In a similar way, the color developer dispersions mentioned in Table 3 were prepared for comparative studies.

TABLE 3

Color developer dispersions (Comparative)

| Dispersion | Compound |
|---|---|
| A-2 | 2,2-bis(4-hydroxyphenyl)propane (Bisphenol A) |
| A-3 | 4,4'-dihydroxydiphenyl sulfone (Bisphenol S) |
| A-4 | 4-isopropoxy-4'-hydroxydiphenyl-sulfone (D8) |

Color Developer Dispersion of Compounds of the Present Application

Preparation of Color Developer Dispersion A-5 (Method D1)

A mixture of 2.5 g 5-(N-3-methylphenyl-sulfonylamido)-(N',N''-bis-(3-methylphenyl)-isophthalic acid-diamide (synthesized according to procedure described in example 4), 1.7 g Gohsenx™ L-3266 (sulfonated polyvinyl alcohol, 10% aqueous solution, Nippon Gohsei) as dispersing aid and binder and 5.8 g demineralized water was milled in a bead mill to an average particle diameter of 1.0 μm to obtain dispersion A-5.

The color developer dispersions mentioned in Table 4 were prepared using method D1.

TABLE 4

Color developer dispersions (Present application) prepared according to method D1

| Dispersion | Compound from example |
|---|---|
| A-6 | 2 |
| A-7 | 6 |
| A-8 | 7 |
| A-9 | 8 |
| A-10 | 9 |
| A-11 | 10 |
| A-12 | 11 |
| A-13 | 12 |
| A-14 | 13 |
| A-15 | 14 |
| A-16 | 15 |
| A-17 | 16 |
| A-18 | 17 |
| A-19 | 18 |
| A-20 | 19 |
| A-21 | 20 |

TABLE 4-continued

| Color developer dispersions (Present application) prepared according to method D1 | |
|---|---|
| Dispersion | Compound from example |
| A-22 | 21 |
| A-23 | 22 |
| A-24 | 23 |
| A-25 | 24 |
| A-26 | 25 |

The preparation of a color developer dispersion was also prepared according to a slightly different formulation.

Preparation of Color Developer Dispersion A-5' (Method D2)

A mixture of 5 g 5-(N-3-methylphenyl-sulfonylamido)-(N',N''-bis-(3-methylphenyl)-isophthalic acid-diamide (=1, 3-Benzenedicarboxylic acid bis-N-(3-methylphenyl)amide-5-sulfonyl-N-(3-methylphenyl)amide) from Ex. 4 (mixture of two crystal forms α+β, 3.34 g Mowiol 4-88 (10% aqueous solution of polyvinyl alcohol MW 31.000, Sigma-Aldrich), 0.1 g of a 45% solution of dispersing agent (sodium salt of naphthalene sulfonic acid condensation product with formalde-hyde, TAMOL® NN 9401 from BASF SE) in water and 11.6 g demineralized water was milled in a bead mill to an average particle diameter of 1.0 μm to obtain dispersion A-5'.

The color developer dispersions mentioned in Table 5 were prepared using method D2.

TABLE 5

| Color developer dispersions (Present application) prepared according to method D2 | |
|---|---|
| Dispersion | Compound from example |
| A-5a' | 4a |
| A-5c' | 4c |
| A-5d' | 4d |
| A-11' | 10a |
| A-13' | 12a |

Preparation of Color Former Dispersion B-1 (Method B1)

A mixture of 5 g of 3-dibutylamino-6-methyl-7-anilnofluoran (Pergascript Black 2C, BASF SE), 10 g of a 10% by weight solution of a polyvinyl alcohol (Mowiol® 40-88, polyvinylalcohol, Mw~205.000 g/mol, Sigma-Aldrich Inc./Kuraray Europe GmbH), 0.1 g of the surfactant 2,4,7,9-tetramethyl-5-decyne-4,7-diol (Aldrich) as 20% solution in isopropanol and 4.9 g of water was milled in a bead mill to an average particle diameter of 1.0 μm to obtain Dispersion B-1.

The color former dispersions mentioned in Table 6 were prepared according to method B1.

TABLE 6

| Color former dispersions prepared according to method B1 | |
|---|---|
| Dispersion | Compound |
| B-2 | 3-(N-ethyl-N-isoamylamino)-6-methyl-7-anilinofluoran (S205) |
| B-3 | 3-(N-ethyl-N-p-tolylamino)-6-methyl-7-anilinofluoran (ETAC) |

The color former dispersion B-1 was also prepared according to a slightly different formulation.

(Method B-1')
Preparation of Color Former Dispersion B-1'.

A mixture of 5 g of 2-anilino-6-dibutylamino-3-methylfluoran (Pergascript Black 2C, BASF SE), 10 g of a 10% by weight aqueous solution of a polyvinyl alcohol (Mowiol 4-88, polyvinylalcohol, Mw~31.000 g/mol, Sigma-Aldrich), 0.1 of 2,4,7,9-tetramethyl-5-decin-4,7-diol, (Aldrich) as 20% solution in isopropanol) and 4.9 g of demineralized water was milled in a bead mill to an average particle diameter of 1.0 μm to obtain Dispersion B-1'.

Preparation of sensitizer dispersion C-1 (Method C1)

A mixture of 5 g of benzyl-2-naphthyl ether (Pergaspeed 305, BASF SE), 0.1 g of a 45% solution of dispersing agent (sodium salt of naphthalene sulfonic acid condensation product with formaldehyde, TAMOL® NN 9401 from BASF SE) in water, 1.7 g of a 10% by weight solution of a polyvinyl alcohol (Mowiol® 40-88 (Polyvinylalcohol, Mw~205.000, Sigma-Aldrich Inc./Ku-raray Europe GmbH) and 13.2 g of water was milled in a bead mill to an average particle diameter of 1.0 μm to obtain Dispersion C-1.

The sensitizer dispersions mentioned in Table 7 were prepared according to method C1.

TABLE 7

| Sensitizer dispersions prepared according to method C1 | |
|---|---|
| Dispersion | Compound |
| C-2 | Stearamide (>90%, TCI) |
| C-3 | Diphenylsulfone (99+%, Alfa Aesar) |
| C-4 | 1,2-Diphenoxyethane (99%, Sigma-Aldrich Inc.) |
| C-5 | Ethyleneglycol-bis(m-tolylether) (KS-232, Sanko Chemical) |

The sensitizer dispersion C-1 was also prepared according to a slightly different formulation.

Preparation of Sensitizer Dispersion C-1' (Method C-1')

A mixture of 5 g of benzyl-2-naphthyl ether (Pergaspeed 305, BASF SE), 0.1 g of a 45% solution of dispersing agent (sodium salt of naphthalene sulfonic acid condensation product with formaldehyde, TAMOL® NN 9401 from BASF SE) in water, 1.7 g of a 10% by weight solution of a polyvinyl alcohol in water (Mowiol® 4-88, Mw~31.000, Sigma-Aldrich Inc.) and 13.2 g of de-mineralized water was milled in a bead mill to an average particle diameter of 1.0 μm to obtain Dispersion C-1', version B.

The sensitizer dispersion mentioned in Table 8 was prepared according to method C-1'

TABLE 8

| Sensitizer dispersion prepared according to method C-1' | |
|---|---|
| Dispersion | Compound |
| C-2' | Stearamide (stearic acid amide, Connect Chemicals) |

Another sensitizer used was bis(p-tolylmethyl) oxalate. The synthesis was performed according to the following procedure:

Synthesis of bis(p-tolylmethyl)oxalate

A mixture comprising 82.3 g (0.33 mol) of 4-methylbenzylalcohol, 97.0 ml (0.69 mol) of triethylamine and 800 ml of toluene was stirred and cooled to 10° C. At this temperature, 28 ml (0.33 mol) of oxalyl chloride was slowly added. After the addition, the reaction mixture was stirred at 20° C. for 2 hours. 100 ml of cold water was added. The formed organic layer was separated and evaporated to dryness. The obtained solid residue was dissolved in 150 ml of n-heptane and heated to 70° C. A clear solution was formed which was allowed to cool to 25° C. The formed precipitate was filtered off and dried.

Yield=65 g, crystalline solid.

$^1$H-NMR (d$_6$-DMSO) δ: 2.3 (s, 6H, Aryl-CH$_3$), 5.2 (s, 4H, OCH$_2$), 7.19 and 7.30 (m, each 4H, Aryl-H) ppm.

The sensitizer dispersion mentioned in Table 9 were prepared according to C-1'.

TABLE 9

Sensitizer dispersions C-3' and C-4'

| Dispersion | Compound |
|---|---|
| C-3' | Bis-(p-tolylmethyl)oxalate |
| C-4' | Ethylene bis(stearamide) (Aldrich) |

Preparation of Filler Dispersion D-1 (Method D-1)

A mixture of 40 g precipitated calcium carbonate (>99%, pro analysis, E. Merck Darmstadt), 0.4 g of an aqueous solution of a dispersing agent (sodium polyacrylate (DISPEX® AA 4140 from BASF SE), pH 7.5, active content 40% by weight), and 59.6 g of water was milled in a bead mill to an average particle diameter of 1.0 grin to obtain Dispersion D-1.

The filler dispersions mentioned in Table 10 were prepared according to method D-1.

TABLE 10

Filler dispersions prepared according to method D-1

| Dispersion | Compound |
|---|---|
| D-2 | Kaoline (Ph. Eur., ~46% SiO$_2$, ~39% Al$_2$O$_3$, Fluka) |
| D-3 | Aluminium trihydroxide (Martinal OL-107, Martinswerk GmbH, Germany) |
| D-4 | amorphous silica (Sipernat ® 350, EVONIK Resource Efficiency GmbH, Germany), solid content reduced to 8.75 g |

The filler dispersion was also prepared according to a slightly different procedure (Method D-1'):

Preparation of Filler Dispersion D-1'

A mixture of 50 g precipitated calcium carbonate (SOCAL P3, Imerys GmbH), 0.5 g of an aqueous solution of a dispersing agent (sodium polyacrylate, DISPEX® N40 from BASF SE), active content 40% by weight), and 49.5 g of water was milled in a bead mill to an average particle diameter of 1.0 μm to obtain Dispersion D-1'.

The filler dispersions mentioned in Table 11 were prepared according to method D-1'.

TABLE 11

Filler dispersions prepared according to method D-1'

| Dispersion | Compound |
|---|---|
| D-2' | Kaoline (Ph. Eur., ~46% SiO$_2$, ~39% Al$_2$O$_3$, Fluka) |
| D-3' | Aluminium hydroxide (Martinal OL-107, Martinswerk GmbH, Germany) |

Preparation of a Sensitizer Dispersion E-1 Containing a Stabilizer (Method E-1)

A mixture of 5 g of benzyl-2-naphthyl ether (Pergaspeed 305, BASF SE), 1.25 g Lowinox CA22 (=Topanol CA, Addivant) as stabilizer, 0.1 g of a 45% solution of dispersing agent (sodium salt of naphthalene sulfonic acid condensation product with formaldehyde, TAMOL® NN 9401 from BASF SE) in water, 1.7 g of a 10% by weight solution of a polyvinyl alcohol in water (Mowiol® 4-88, Mw~31.000, Sigma-Aldrich Inc.) and 13.2 g of demineralized water was milled in a bead mill to an average particle diameter of 1.0 μm to obtain dispersion E1.

Another stabilizer used was 1,1,3-Tris(3-cyclohexyl-4'-hydroxy-6-methylphenyl) butane. This compound was synthesized according to a known procedure.

Synthesis of 1,1,3-tris(3-cyclohexyl-4'-hydroxy-6-methylphenyl)butane 30 g (0.157 mol) of cyclohexyl-5-methylphenol and 3.86 g (0.055 mol) of crotonaldehyde in methanol (60 ml) was reacted while passing HCl gas as described in EP0230961. A dark reaction mass was obtained which solidified.

To the thick reaction mass, water was added to obtain a suspension. The precipitate was collected by filtration and washed with water. Then wet product was taken up in 150 ml of a mixture of 10% ethyl acetate: heptane (1:10) and stirred for 15 min. The precipitate was filtered off and dried. Yield 65 g, white solid.

$^1$H-NMR (d$_6$-DMSO) δ: 0.8-2.2 and 2.6-2.9 (m; totally 49H, aliphatic H), 6.4 (m; 3H, Aryl-H), 6.8, 6.9 and 7.1 (s; each 1H, Aryl H, 8.80 (s; 3H, OH) ppm.

Following the same formulation as described for E-1, a sensitizer suspension containing 1,1,3-tris(3-cyclohexyl-4'-hydroxy-6-methylphenyl)butane was prepared.

Another stabilizer used was the reaction product of 4,4'-sulfonylbis(benzeneamine), 2,4-toluenediisocyanate and phennol which is commercially available from Asahi Kasei Corp under the tradename UU.

The sensitizer dispersions containing a stabilizer mentioned in Table 12 were prepared according to method E-1

TABLE 12

Sensitizer dispersion containing a stabilizer prepared according to method E-1

| Stabilizer | Compound |
|---|---|
| E-1 | Lowinox CA22 (=Topanol CA, Addivant) |
| E-2 | 1,1,3-tris(3-cyclohexyl-4'-hydroxy-6-methylphenyl)butane |
| E-3 | UU (Asahi Kasei Corp.) |

VI) Application Examples: Preparation of Heat Sensitive Coated Paper

Application Example 1: Preparation of a Heat-Sensitive Recording Layer Coating Compositions Method A 80 g of dispersion A-1, 40 g of dispersion B-1, 80 g of dispersion C-1, 75 g of dispersion D-1, 135 g of a 10% by weight aqueous solution of a polyvinyl alcohol (Mowiol® 4-98, polyvinylalcohol, Mw~205.000 g/mol, Sigma-Aldrich Inc./Kuraray Europe GmbH) and 20.6 g of a 17% aqueous dispersion of zinc stearate (Hidorin® F115 from Chukyo Europe) were mixed and stirred to obtain a heat sensitive recording layer coating composition.

A base paper coated with calcined kaolin (Ansilex® 93 from BASF SE, coat weight 7 g/m$^2$) was coated with the above heat sensitive recording layer coating composition using a #2 wire bar (12 μm wet thickness) and dried at room temperature. The resulting heat sensitive recording layer coating composition was calendered to obtain a smooth surface.

Application example 1 was repeated with different components to yield additional heat sensitive recording layer coating compositions. Table 13 summarizes the different compositions used.

The heat sensitive coated papers prepared using the various the color developer dispersions of the present application are mentioned in Table 13.

TABLE 13

Heat sensitive coated papers prepared according to method A

| Application example | Color developer |
|---|---|
| AEx-2 | A-2 |
| AEx-3 | A-3 |
| AEx-4 | A-4 |
| AEx-5 | A-5 |
| AEx-6 | A-6 |
| AEx-7 | A-7 |
| AEx-8 | A-8 |
| AEx-9 | A-9 |
| AEx-10 | A-10 |
| AEx-11 | A-11 |
| AEx-12 | A-12 |
| AEx-13 | A-13 |
| AEx-14 | A-14 |
| AEx-15 | A-15 |
| AEx-16 | A-16 |
| AEx-17 | A-17 |
| AEx-18 | A-18 |
| AEx-19 | A-19 |
| AEx-20 | A-20 |
| AEx-21 | A-21 |
| AEx-22 | A-22 |
| AEx-23 | A-23 |
| AEx-24 | A-24 |
| AEx-25 | A-25 |
| AEx-26 | A-26 |

Application Example 27:

80 g of dispersion A-11, 40 g of dispersion B-1, 80 g of dispersion C-5, 75 g of dispersion D-1, 135 g of a 10% by weight aqueous solution of a polyvinyl alcohol (Mowiol® 4-98, polyvinyl alcohol, Mw~205.000 g/mol, Sigma-Aldrich Inc/Kuraray Europe GmbH) and 20.6 g of a 17% aqueous dispersion of zinc stearate (Hidorin® F115 from Chukyo Europe) were mixed and stirred to obtain a heat sensitive recording layer coating composition.

A base paper was coated, dried and calendered as described in Application Example 1.

Application example 27 was repeated with different components to yield additional heat sensitive recording layer coating compositions. Table 14 summarizes the different compositions used.

TABLE 14

Heat sensitive coated papers prepared according to method A

| Application example | Color developer | Sensitizer |
|---|---|---|
| AEx-28 | A-5 | C-5 |
| AEx-29 | A-6 | C-5 |
| AEx-30 | A-18 | C-5 |
| AEx-31 | A-19 | C-5 |
| AEx-32 | A-13 | C-5 |
| AEx-33 | A-2 | C-5 |
| AEx-34 | A-24 | C-5 |
| AEx-35 | A-5 | C-2 |
| AEx-36 | A-5 | C-3 |

In a similar way, the heat sensitive coated papers mentioned in Table 15 were prepared with different dispersion compositions and color developers.

TABLE 15

Heat sensitive coated papers prepared according to method A

| Application example | Color former No. | amount | Color developer No. | amount | Sensitizer No. | amount | Filler No. | amount | OBA amount |
|---|---|---|---|---|---|---|---|---|---|
| AEx-37 | B-1 | 40 | A-5 | 80 | C-1 | 80 | D-1 | 75 | — |
| AEx-38 | B-1 | 40 | A-5 | 80 | C-1 | 80 | D-2 | 75 | — |
| AEx-39 | B-1 | 40 | A-5 | 80 | C-1 | 80 | D-3 | 75 | — |
| AEx-40 | B-1 | 40 | A-5 | 80 | C-1 | 80 | D4 | 75 | — |
| AEx-41 | B-2 | 40 | A-5 | 80 | C-1 | 80 | D-1 | 75 | |
| AEx-42 | B-1 | 20 | A-5 | 80 | C-1 | 80 | D-1 | 75 | — |
| | B-2 | 20 | | | | | | | |
| AEx-43 | B-1 | 24 | A-5 | 80 | C-1 | 80 | D-1 | 75 | — |
| | B-2 | 16 | | | | | | | |
| AEx-44 | B-1 | 40 | A-5 | 80 | C-2 | 80 | D-1 | 75 | — |
| AEx-45 | B-1 | 40 | A-5 | 80 | C-3 | 80 | D-1 | 75 | |
| AEx-46 | B-1 | 40 | A-5 | 80 | C-4 | 80 | D-1 | 75 | — |
| AEx-47 | B-3 | 40 | A-5 | 120 | C-1 | 80 | D-1 | 75 | — |
| AEx-48 | B-3 | 40 | A-5 | 120 | C-1 | 80 | D-3 | 75 | — |
| AEx-49 | B-1 | 40 | A-5 | 80 | C-1 | 80 | D-1 | 75 | 1.4 * |

* Tinopal ® ABP-X HC new (BASF India Ltd.) was used as optical brightening agent and added as is to the final heat sensitive coating composition.

Amounts mentioned in the table are parts by weight.

Application Example 50: Preparation of a Heat-Sensitive Recording Layer Coating Compositions 80 g of dispersion A-5a', 40 g of dispersion B-1', 80 g of dispersion C-1', 63 g of dispersion D-1', 130 g of a 10% by weight aqueous solution of a polyvinyl alcohol (Mowiol® 4-98, polyvinyl alcohol, Mw~27.000 g/mol, Sigma-Aldrich Inc.) and 29.4 g of a 17% aqueous dispersion of zinc stearate (Hidorin® F115 from Chukyo Europe) were mixed and stirred to obtain a heat sensitive recording layer coating composition.

A base paper (coat weight 8 g/m²) was coated with the above heat sensitive recording layer coating composition using a #7 wire bar (75 µm wet thickness) and dried at room temperature. The resulting heat sensitive recording layer coating composition was calendered to obtain a smooth surface.

In a similar way, the heat sensitive coated papers mentioned in Table 16 were prepared by either exchanging the color developer dispersion A-5a' by the color developer dispersion or by changing the sensitizer C'1 by another sensitizer or a mixture of sensitizers or by changing the filler D1' by another filler. Heat sensitive coated papers were also made by the addition of optical brighteners.

To each of the above Application examples 61, 62, 71 and 71 were added 130 g of a 10% by weight aqueous solution of a polyvinyl alcohol (Mowiol® 4-98, polyvinyl alcohol, Mw 27.000 g/mol, Sigma-Aldrich Inc.) and 29.4 g of a 17% aqueous dispersion of zinc stearate (Hidorin® F 115 from Chukyo Europe), mixed and stirred to obtain a heat sensitive recording layer coating composition.

A base paper (coat weight 8 g/m²) was coated and dried according to the procedure given in Application example 50. The resulting heat sensitive recording layer coating composition was calendered to obtain a smooth surface.

VI) Application Examples: Evaluation of Heat Sensitive Recording Materials

The heat sensitive recording materials prepared according to the invention were evaluated as described below and the results of the evaluations are summarized in Tables 18-A.

Image Optical Density

Using a Thermal Tester (Atlantek Model 400 manufactured by Atlantek Inc.), each heat sensitive recording material was printed at an applied energy of 30 mJ/mm² and the density of the recorded image thus obtained was measured with a GretagMacbeth™ eyeone pro densitometer.

TABLE 16

Heat sensitive coated papers prepared according to application example 50

| Application example | Color former No. | amount | Color developer No. | amount | Sensitizer No. | amount | Filler No. | amount | OBA amount |
|---|---|---|---|---|---|---|---|---|---|
| AEx-50 | B-1' | 40 | A-5a' | 80 | C-1' | 80 | D-1' | 63 | — |
| AEx-51 | B-1' | 40 | A-5' | 80 | C-1' | 80 | D-1' | 63 | — |
| AEx-52 | B-1' | 40 | A-5c' | 80 | C-1' | 80 | D-1' | 63 | — |
| AEx-53 | B-1' | 40 | A-5' | 80 | C-2' | 80 | D-1' | 63 | — |
| AEx-54 | B-1' | 40 | A-5a' | 80 | C-2' | 80 | D-1' | 63 | — |
| AEx-55 | B-1' | 40 | A-5' | 80 | C-1' | 80 | D-2' | 63 | — |
| AEx-56 | B-1' | 40 | A-5' | 80 | C-1' | 80 | D-2' | 63 | — |
| AEx-57 | B-1' | 40 | A-5d' | 80 | C-1' | 80 | D-1' | 63 | — |
| AEx-58 | B-1' | 40 | A-6' | 80 | C-1' | 80 | D-1' | 63 | — |
| AEx-59 | B-1' | 40 | A-11' | 80 | C-1' | 80 | D-1' | 63 | — |
| AEx-60 | B-1' | 40 | A-13' | 80 | C-1' | 80 | D-1' | 63 | — |
| AEx-63 | B-1' | 40 | A-5d' | 80 | C-2' | 80 | D-1' | 63 | — |
| AEx-64 | B-1' | 40 | A-5d' | 80 | C-3' | 80 | D-1' | 63 | — |
| AEx-65 | B-1' | 40 | A-5d | 80 | C-2" | 80 | D-2' | 63 | — |
| AEx-66 | B-1' | 40 | A-5d' | 80 | C-(1 + 2)' | 80 | 40 C-1 D-1' 40 C-2 | 63 | — |
| AEx-67 | B-1' | 40 | A-5d' | 80 | C-4' | 80 | D-1' | 63 | — |
| AEx-68 | B-1' | 40 | A-5d' | 80 | C2" | 80 | D-3' | 63 | — |
| AEx-69 | B-1' | 40 | A-5d' | 80 | C-2" | 80 | D-1' | 63 | 1.4* |
| AEx-70 | B-1' | 40 | A-5d' | 80 | C-1' | 80 | D-1' | 63 | 1.4* |

*Tinopal ® ABP-Z liquid (22% aqueous solution, BASF India Ltd.) was used as optical brightening agent and added as is to the final heat sensitive coating composition.
Amounts mentioned in the table are parts by weight.

Heat sensitive coated papers were also prepared by the addition of stabilizers E-1 or E-2 are mentioned in Table 17.

TABLE 17

Heat sensitive coated papers containing stabilizers E-1, E-2 or E3

| Application example | Color former No. | amount | Color developer No. | amount | Sensitizer No. | amount | Filler No. | amount | Stabilizer No | amount |
|---|---|---|---|---|---|---|---|---|---|---|
| AEx-61 | B-1' | 40 | A-5d' | 80 | C-1' | 80 | D-1' | 60 | E-1 | 20 |
| AEx-62 | B-1' | 40 | A-5d' | 80 | C-1' | 80 | D-1' | 60 | E-2 | 20 |
| AEx-71 | B-1' | 40 | A-5d' | 80 | C-2' | 80 | D-1' | 60 | E-3 | 20 |
| A-Ex-72 | B-1' | 40 | A-5d' | 80 | C-1' | 80 | D-1' | 60 | E-3 | 20 |

Background

The optical density of the unrecorded portion of the heat sensitive material was measured with a densitometer (GretagMacbeth™ eyeone pro densitometer).

Heat Resistance

After printing, the heat sensitive recording material was stored for 24 hours in an oven at a temperature of 60° C. The optical densities of the recorded and unrecorded portions were then measured with the above densitometer.

Heat/Humidity Resistance

After printing, the heat sensitive recording material was stored for 24 hours in an oven at a temperature of 40° C. and 90% relative humidity. The optical densities of the recorded and unrecorded portions were then measured with the above densitometer.

Light Resistance

After printing, the heat sensitive recording material was stored for 4.5 hours in a xenon weatherometer (Atlas Suntester GPS+, 1000 W/m$^2$). The optical densities of the recorded and unrecorded portions were then measured with the above densitometer.

Oil Resistance

After printing, the heat sensitive recording material was coated using a #2 wire bar (12 μm wet thickness) with cottonseed oil and then stored for 24 hours in an oven at a temperature of 40° C. The optical density of the recorded portion was then measured with the above densitometer.

TABLE 18

Part 1: Evaluation of heat sensitive recording material using benzyl-2-naphthyl ether as sensitizer

| Appl. example | Optical density (recorded portion) | Optical density (unrecorded portion) | Heat resistance (recorded portion) | Heat resistance (unrecorded portion) |
|---|---|---|---|---|
| AEx-1 | 1.41 | 0.05 | 1.35 (96%) | 0.1 |
| AEx-2 | 1.28 | 0.05 | 1.11 (87%) | 0.13 |
| AEx-3 | 1.51 | 0.07 | 1.32 (87%) | 0.09 |
| AEx-4 | 1.52 | 0.06 | 1.39 (91%) | 0.12 |
| AEx-5 | 0.91 | 0.03 | 0.53 (58%) | 0.06 |
| AEx-6 | 1.37 | 0.08 | 1.20 (88%) | 0.11 |
| AEx-7 | 1.43 | 0.13 | 1.32 (92%) | 0.4 |
| AEx-11 | 1.16 | 0.04 | 1.24 (107%) | 0.11 |
| AEx-13 | 1.20 | 0.05 | 1.18 (98%) | 0.07 |
| AEx-14 | 0.86 | 0.05 | 0.19 (22%) | 0.07 |
| AEx-18 | 1.24 | 0.09 | 1.20 (97%) | 0.1 |
| AEx-19 | 1.49 | 0.11 | 1.48 (99%) | 1.04 |
| AEx-20 | 1.41 | 0.1 | 1.51 (93%) | 0.58 |
| AEx-21 | 1.37 | 0.15 | 1.42 (104%) | 0.78 |
| AEx-22 | 1.31 | 0.05 | 0.58 (44%) | 0.06 |

TABLE 18

Part 2: Evaluation of heat sensitive recording material using benzyl-2-naphthyl ether as sensitizer

| Appl. example | Heat/ humidity resistance (recorded portion) | Heat/ humidity resistance (unrecorded portion) | Light resistance (recorded portion) | Light resistance (unrecorded portion) | Oil resistance (recorded portion) |
|---|---|---|---|---|---|
| AEx-1 | 1.26 (89%) | 0.13 | 1.33 (94%) | 0.15 | 1.47 (104%) |
| AEx-2 | 1.23 (96%) | 0.08 | 1.11 (87%) | 0.10 | 0.98 (77%) |
| AEx-3 | 1.19 (79%) | 0.11 | 1.58 (105%) | 0.18 | 1.03 (68%) |
| AEx-4 | 1.39 (91%) | 0.08 | 1.54 (101%) | 0.15 | 0.31 (20%) |
| AEx-5 | — | — | 1.06 (116%) | 0.11 | — |
| AEx-6 | 1.27 (93%) | 0.09 | 1.35 (98%) | 0.15 | 1.22 (89%) |
| AEx-7 | 1.48 (103%) | 0.33 | 1.52 (106%) | 0.45 | — |
| AEx-11 | — | — | 1.28 (110%) | 0.13 | 1.15 (99%) |
| AEx-13 | 0.80 (67%) | 0.05 | 1.18 (98%) | 0.18 | 1.04 (87%) |
| AEx-14 | 0.13 (15%) | 0.07 | 0.95 (110%) | 0.15 | 0.14 (16%) |
| AEx-18 | 1.30 (105%) | 0.11 | 1.37 (110%) | 0.18 | 0.97 (78%) |
| AEx-19 | 1.43 (96%) | 0.45 | 1.49 (100%) | 0.16 | 0.73 (49%) |
| AEx-20 | 1.36 (96%) | 0.33 | 1.43 (101%) | 0.29 | — |
| AEx-21 | 1.41 (103%) | 0.54 | 1.43 (104%) | 0.29 | — |
| AEx-22 | — | — | 1.41 (108%) | 0.13 | — |

TABLE 19

Part 1: Evaluation of heat sensitive recording material using ethylene glycol-bis-m-tolylether, stearylamide or diphenyl sulfone as sensitizer

| Appl. example | Optical density (recorded portion) | Optical density (unrecorded portion) | Heat resistance (recorded portion) | Heat resistance (unrecorded portion) |
|---|---|---|---|---|
| AEx-27 | 1.2  | 0.04 | 0.3 (25%)   | 0.13 |
| AEx-28 | 0.86 | 0.04 | 0.32 (37%)  | 0.05 |
| AEx-29 | 1.22 | 0.04 | 0.92 (75%)  | 0.06 |
| AEx-30 | 1.24 | 0.09 | 0.99 (80%)  | 0.12 |
| AEx-31 | 1.42 | 0.13 | 1.43 (101%) | 0.89 |
| AEx-32 | 1.03 | 0.05 | 0.99 (96%)  | 0.06 |
| AEx-33 | 1.52 | 0.10 | 1.15 (76%)  | 0.27 |
| AEx-34 | 0.80 | 0.04 | 1.17 (146%) | 0.11 |
| AEx-35 | 0.80 | 0.03 | 0.60 (75%)  | 0.05 |
| AEx-36 | 0.88 | 0.04 | 0.46 (52%)  | 0.05 |

TABLE 19

Part 2: Evaluation of heat sensitive recording material using ethylene glycol-bis-m-tolylether, stearylamide or diphenyl sulfone as sensitizer

| Appl. example | Heat/humidity resistance (recorded portion) | Heat/humidity resistance (unrecorded portion) | Light resistance (recorded portion) | Light resistance (unrecorded portion) | Oil resistance (recorded portion) |
|---|---|---|---|---|---|
| AEx-27 | 0.88 (73%)  | 0.08 | 1.31 (109%) | 0.13 | 1.10 (92%)  |
| AEx-28 | —           | —    | 1.05 (122%) | 0.13 | 0.15 (17%)  |
| AEx-29 | 0.91 (74%)  | 0.05 | 1.24 (102%) | 0.11 | 0.28 (23%)  |
| AEx-30 | 1.15 (93%)  | 0.09 | 1.24 (100%) | 0.17 | 0.19 (15%)  |
| AEx-31 | 1.37 (96%)  | 0.32 | 1.47 (103%) | 0.13 | 1.46 (103%) |
| AEx-32 | 0.81 (79%)  | 0.05 | 1.18 (115%) | 0.16 | 0.80 (78%)  |
| AEx-33 | 1.15 (76%)  | 0.16 | 1.50 (99%)  | 0.17 | 0.26 (17%)  |
| AEx-34 | 1.09 (136%) | 0.09 | 1.25 (156%) | 0.18 | —           |
| AEx-35 | 0.53 (66%)  | 0.04 | 0.89 (111%) | 0.13 | 0.13 (16%)  |
| AEx-36 | 0.41 (46%)  | 0.04 | 1.04 (118%) | 0.13 | 0.11 (12%)  |

TABLE 20

Part 1: Investigation of the influence of different coating components on the performance of 5-(N-3-methylphenyl-sulfonylamido)-(N',N''-bis-(3-methylphenyl)-isophthalic acid-diamide as sensitizer as made in example 4.

| Appl. example | Optical density (recorded portion) | Optical density (unrecorded portion) | Heat resistance (recorded portion) | Heat resistance (unrecorded portion) |
|---|---|---|---|---|
| AEx-37 | 1.33 | 0.10 | 1.20 (90%) | 0.14 |
| AEx-38 | 1.32 | 0.11 | 1.14 (86%) | 0.13 |
| AEx-39 | 1.35 | 0.10 | 1.20 (89%) | 0.14 |
| AEx-40 | 1.29 | 0.10 | 1.12 (87%) | 0.16 |
| AEx-41 | 1.33 | 0.10 | 1.25 (94%) | 0.14 |
| AEx-42 | 1.35 | 0.11 | 1.25 (92%) | 0.17 |
| AEx-43 | 1.38 | 0.12 | 1.25 (91%) | 0.18 |
| AEx-44 | 1.35 | 0.09 | 1.28 (95%) | 0.11 |
| AEx-45 | 1.34 | 0.09 | 1.24 (93%) | 0.14 |
| AEx-46 | 1.40 | 0.09 | 1.14 (81%) | 0.11 |
| AEx-47 | 1.25 | 0.06 | 0.92 (74%) | 0.08 |
| AEx-48 | 1.14 | 0.08 | 0.93 (81%) | 0.09 |
| AEx-49 | 1.37 | 0.08 | 1.20 (88%) | 0.11 |

TABLE 20

Part 2:

| Appl. example | Heat/humidity resistance (recorded portion) | Heat/humidity resistance (unrecorded portion) | Light resistance (recorded portion) | Light resistance (unrecorded portion) | Oil resistance (recorded portion) |
|---|---|---|---|---|---|
| AEx-37 | 1.28 | 0.11 | 1.39 | 0.09 | 1.22 |
| AEx-38 | 1.28 | 0.10 | 1.33 | 0.11 | 1.32 |
| AEx-39 | 1.29 | 0.10 | 1.33 | 0.11 | 1.44 |
| AEx-40 | 1.19 | 0.10 | 1.27 | 0.10 | 0.52 |
| AEx-41 | 1.26 | 0.12 | 1.35 | 0.12 | 1.12 |
| AEx-42 | 1.30 | 0.13 | 1.35 | 0.14 | 1.44 |
| AEx-43 | 1.31 | 0.14 | 1.39 | 0.14 | 1.00 |
| AEx-44 | 1.28 | 0.11 | 1.31 | 0.16 | 0.71 |
| AEx-45 | 1.27 | 0.10 | 1.36 | 0.15 | 1.41 |
| AEx-46 | 1.31 | 0.08 | 1.37 | 0.13 | 1.24 |
| AEx-47 | 0.99 | 0.06 | 1.21 | 0.11 | 0.43 |
| AEx-48 | 0.94 | 0.06 | 1.19 | 0.12 | 0.41 |
| AEx-49 | 1.27 | 0.09 | 1.35 | 0.08 | 1.22 |

TABLE 21

Part 1:

| Appl. example | Optical density (recorded portion) | Optical density (unrecorded portion) | Heat resistance (recorded portion) | Heat resistance (unrecorded portion) |
|---|---|---|---|---|
| AEx-50 | 1.34 | 0.08 | 1.05 | 0.09 |
| AEx-51 | 1.35 | 0.07 | 1.33 | 0.08 |
| AEx-52 | 1.37 | 0.09 | 1.19 | 0.11 |
| AEx-53 | 1.42 | 0.09 | 1.34 | 0.10 |
| AEx-54 | 1.43 | 0.07 | 1.34 | 0.08 |
| AEx-55 | 1.37 | 0.08 | 1.22 | 0.11 |
| AEx-56 | 1.38 | 0.08 | 1.29 | 0.09 |
| AEx-57 | 1.31 | 0.06 | 1.23 | 0.13 |

TABLE 21-continued

Part 1:

| Appl. example | Optical density (recorded portion) | Optical density (unrecorded portion) | Heat resistance (recorded portion) | Heat resistance (unrecorded portion) |
|---|---|---|---|---|
| AEx-58 | 1.11 | 0.05 | 0.29 | 0.11 |
| AEx-59 | 0.61 | 0.05 | 0.81 | 0.18 |
| AEx-60 | 1.01 | 0.07 | 1.43 | 0.12 |
| AEx-61 | 1.35 | 0.07 | 1.37 | 0.07 |
| AEx-62 | 1.36 | 0.07 | 1.34 | 0.37 |
| AEx-63 | 1.34 | 0.08 | 1.33 | 0.17 |
| AEx-64 | 1.42 | 0.1 | 1.31 | 0.1 |
| AEx-65 | 1.41 | 0.14 | 1.37 | 0.22 |
| AEx-66 | 1.39 | 0.13 | 1.24 | 0.15 |
| AEx. 67 | 1.25 | 0.07 | 1.21 | 0.08 |
| AEx. 68 | 1.30 | 0.08 | 1.27 | 0.09 |
| AEx. 69 | 1.36 | 0.07 | 1.37 | 0.15 |
| AEx. 70 | 1.38 | 0.07 | 1.32 | 0.08 |
| AEx. 71 | 1.33 | 0.08 | 1.30 | 0.29 |
| AEx. 72 | 1.39 | 0.1 | 1.39 | 0.31 |

TABLE 21

Part 2:

| Appl. example | Heat/humidity* resistance (recorded portion) | Heat/humidity resistance (unrecorded portion) | Light resistance (recorded portion) | Light resistance (unrecorded portion) | Oil resistance (recorded portion) |
|---|---|---|---|---|---|
| AEx-50 | 1.28 | 0.08 | 1.34 | 0.15 | 0.46 |
| AEx-51 | 1.34 | 0.08 | 1.35 | 0.17 | 0.34 |
| AEx-52 | 1.30 | 0.08 | 1.37 | 0.19 | 0.95 |
| AEx-53 | 1.39 | 0.09 | 1.39 | 0.17 | 0.29 |
| AEx-54 | 1.37 | 0.07 | 1.38 | 0.14 | 0.41 |
| AEx-55 | 1.39 | 0.09 | 1.40 | 0.17 | 0.51 |
| AEx-56 | 1.46 | 0.11 | 1.35 | 0.15 | 0.90 |
| AEx-57 | 1.27 | 0.06 | 1.35 | 0.15 | 0.88 |
| AEx-58 | 0.99 | 0.06 | 1.06 | 0.06 | 0.22 |
| AEx-59 | 0.59 | 0.05 | 0.96 | 0.15 | 0.75 |
| AEx-60 | 1.26 | 0.08 | 1.34 | 0.23 | 1.06 |
| AEx-61 | 1.33 | 0.09 | 1.36 | 0.15 | 1.32 |
| AEx-62 | 1.33 | 0.1 | 1.37 | 0.15 | 1.29 |
| AEx-63 | 1.33 | 0.12 | 1.37 | 0.2 | 0.74 |
| AEx-64 | 1.31 | 0.1 | 1.43 | 0.19 | 0.94 |
| AEx-65 | 1.40 | 0.15 | 1.35 | 0.15 | 1.39 |
| AEx-66 | 1.30 | 0.16 | 1.41 | 0.21 | 0.86 |
| AEx.-67 | 1.20 | 0.09 | 1.22 | 0.16 | 0.81 |
| AEx.-68 | 1.24 | 0.08 | 1.25 | 0.18 | 0.92 |
| AEx.-69 | 1.33 | 0.08 | 1.35 | 0.15 | 1.17 |
| AEx. 70 | 1.32 | 0.08 | 1.34 | 0.14 | 1.18 |
| AEx. 71 | 1.27 | 0.14 | n.d. | n.d. | 1.28 |
| AEx. 72 | 1.40 | 0.16 | n.d. | n.d. | 1.38 |

The invention claimed is:

1. A compound of formula (I)

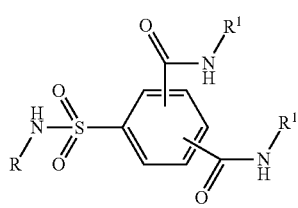

(I)

wherein
R and $R^1$ are independently selected from the group of linear or branched $C_1$-$C_{18}$-alkyl,
$R^{11}$O-$R^{12}$— wherein $R^{11}$ and $R^{12}$ are independently linear or branched $C_1$-$C_8$-alkyl,
$(R^{13})_2$N—$R^{12}$— wherein $R^{13}$ is a linear or branched $C_1$-$C_8$-alkyl or together with the nitrogen to which they are attached form a 5 or 6 membered ring, and
a radical of formula (II)

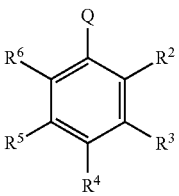

(II)

wherein, $R^2$, $R^3$, $R^4$, $R^5$, and $R^6$ are independently selected from the group of hydrogen,
linear or branched $C_1$-$C_8$-alkyl,
—NH—C(=O)—$R^{14}$,   —C(=O)—NH—$R^{14}$, wherein $R^{14}$ is linear or branched $C_1$-$C_8$-alkyl,
—C(=O)O$R^{15}$, wherein $R^{15}$ is linear or branched $C_1$-$C_8$-alkyl, and
halogen, or
$R^2$ and $R^3$, or $R^4$ and $R^5$ or both, or
$R^3$ and $R^4$, or $R^5$ and $R^6$ or both, or
$R^2$ and $R^3$ as well as $R^5$ and $R^6$ together form a hydrocarbon diradical comprising 3 or 4 carbon atoms;

and

Q is a single bond or branched or unbranched $C_1$-$C_8$-alkylene, optionally comprising one or more oxygen atoms;

with the proviso that at least one of R or $R^1$ is a radical of formula (II).

2. The compound according to claim 1,

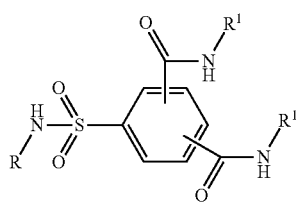

wherein
R and $R^1$ are independently
a radical of formula (II)

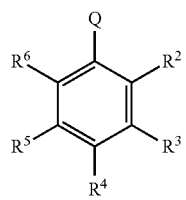

wherein, $R^2$, $R^3$, $R^4$, $R^5$, and $R^6$ are independently selected from the group of
hydrogen, and
linear or branched $C_1$-$C_8$-alkyl,
and
Q is a single bond.

3. The compound according to claim 1 wherein the compound is of formula (III)

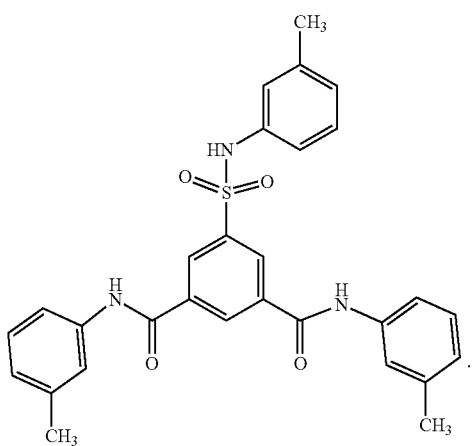

4. The compound according to claim 3, wherein the compound is a crystalline polymorph form α that is characterized by an X-ray powder diffraction pattern comprising 2Θ reflections, plus or minus 0.2 degrees 2Θ0, at 5.5, 6.1, 6.4, 12.1, 16.1, 16.8, 17.1, 18.3, 19.1, 19.9, 20.2, 21.4, 22.1, 22.7, 23.3, 24.3, 24.7, 25.0, 26.4, 27.7 and 29.3.

5. The compound according to claim 3, wherein the compound is a crystalline polymorph form β that is characterized by an X-ray powder diffraction pattern comprising 2Θ reflections, plus or minus 0.2 degrees 2Θ, at 6.2, 8.1, 10.1, 11.8, 12.2, 13.4, 14.1, 15.3, 16.1, 17.2, 18.4, 19.1, 20.6, 21.4, 22.4, 24.5, 25.0, 25.9, 26.2, 26.9 and 28.4.

6. A process for preparing a compound according to claim 1 comprising the following steps,
a) chlorinating a sulfo-isophthalic compound (IVa) with a chlorination agent to obtain an acid chloride of formula (IVb),

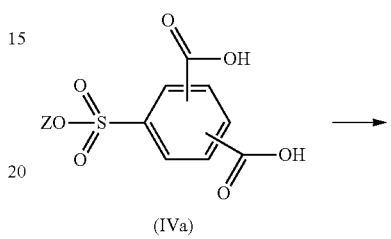

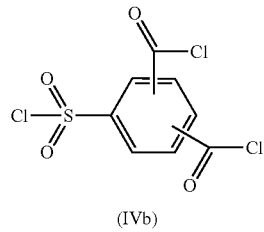

wherein Z stands for hydrogen or an alkali metal;
b) optionally, isolating the acid chloride (IVb);
c) reacting the acid chloride (IVb) with at least one amine to obtain the compound of formula (I).

7. The process according to claim 6, wherein the chlorination agent is selected from the group of thionyl chloride, $POCl_3$, $PCl_5$ and oxalyl chloride.

8. The process according to claim 6, wherein acid chloride (IVb) is 5-sulfonylchloride-isophthalic acid dichloride.

9. The process according to claim 6, wherein the at least one amine is selected from the group of
linear or branched $C_1$-$C_{18}$-alkylamine,
$R^{11}O$—$R^{12}$—$NH_2$, wherein $R^{11}$ and $R^{12}$ are independently linear or branched $C_1$-$C_8$-alkyl,
$(R^{13})_2N$—$R^{12}$—$NH_2$, wherein $R^{13}$ is a linear or branched $C_1$-$C_8$-alkyl or together with the nitrogen to which they are attached form a 5 or 6 membered ring, and
an amine of formula (IIa)

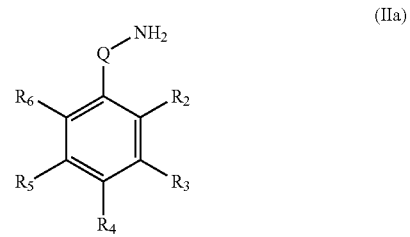

wherein, $R^2$, $R^3$, $R^4$, $R^5$, and $R^6$ are independently selected from the group of
hydrogen,
linear or branched $C_1$-$C_8$-alkyl, —NH—C(=O)—R$^{14}$, —C(=O)—NH—R$^{14}$,
wherein R$^{14}$ is linear or branched C$_1$-C$_8$-alkyl,
—C(=O)OR$^{15}$, wherein R$^{15}$ is linear or branched C$_1$-C$_8$-alkyl, and
halogen, or
R$^2$ and R$^3$, or R$^4$ and R$^5$ or both, or
R$^3$ and R$^4$, or R$^5$ and R$^6$ or both, or
R$^2$ and R$^3$ as well as R$^5$ and R$^6$ together form a hydrocarbon diradical comprising 3 or 4 carbon atoms;
and
Q is a single bond or branched or unbranched C$_1$-C$_8$-alkylene, optionally comprising one or more oxygen atoms,
with the proviso that at least one of R or R$^1$ is a radical of formula (II) in the product of formula (I).

10. The process according to claim 6, wherein step c) comprises reacting the acid chloride of formula (IVb) with an amine RNH$_2$ to obtain a compound of formula (I), wherein R$^1$ is identical to R.

11. The process according to claim 6, wherein the amine is m-toluidine.

12. The process according to claim 6, wherein step c) comprises the following sub-steps,
i) reacting an acid chloride of formula (IVb) with a first amine R$^1$NH$_2$ to obtain a compound of formula (V),

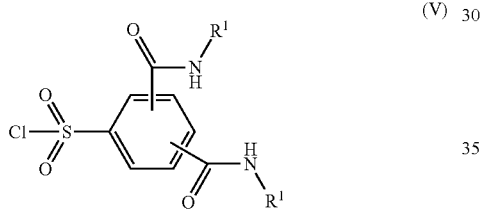 (V)

ii) reacting the product obtained in substep i) with a second amine RNH$_2$ to obtain a compound of formula (I) wherein R and R$^1$ are different.

13. A heat sensitive recording material comprising
A) at least one color former, and
B) at least one color developer of formula (I)

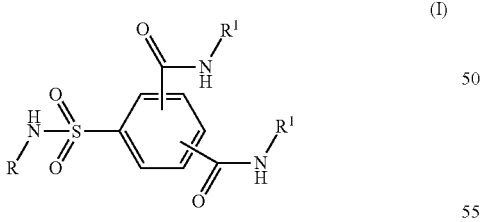 (I)

wherein R and R$^1$ are defined as in claim 1.

14. The heat sensitive recording material according to claim 13, wherein the weight ratio of color developer to color former is in the range of 1.5:1 to 3:1.

15. The heat sensitive recording material according to claim 13 further comprising at least one sensitizer.

16. The heat sensitive recording material according to claim 15, wherein the weight ratio of color developer to sensitizer is in the range of 0.5:1 to 1.5:1.

17. The heat sensitive recording material according to claim 13 further comprising at least one stabilizer.

18. The compound according to claim 1, wherein R and R$^1$ are independently selected from the group of
—R$^{11}$O—R$^{12}$— wherein R$^{11}$ and R$^{12}$ are independently linear or branched C$_1$-C$_8$-alkyl,
—(R$^{13}$)$_2$N—R$^{12}$— wherein R$^{13}$ is a linear or branched C$_1$-C$_8$-alkyl or together with the nitrogen to which they are attached form a 5 or 6 membered ring, and
a radical of formula (II)

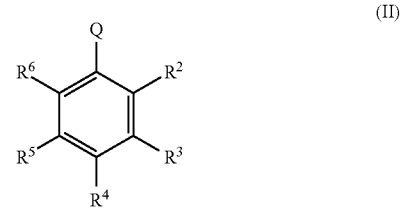 (II)

wherein, R$^2$, R$^3$, R$^4$, R$^5$, and R$^6$ are independently selected from the group of
hydrogen,
linear or branched C$_1$-C$_8$-alkyl,
—NH—C(=O)—R$^{14}$, —C(=O)—NH—R$^{14}$,
wherein R$^{14}$ is linear or branched C$_1$-C$_8$-alkyl,
—C(=O)OR$^{15}$, wherein R$^{15}$ is linear or branched C$_1$-C$_8$-alkyl, and
halogen, or
R$^2$ and R$^3$, or R$^4$ and R$^5$ or both, or
R$^3$ and R$^4$, or R$^5$ and R$^6$ or both, or
R$^2$ and R$^3$ as well as R$^5$ and R$^6$ together form a hydrocarbon diradical comprising 3 or 4 carbon atoms;
and
Q is a single bond or branched or unbranched C$_1$-C$_8$-alkylene, optionally comprising one or more oxygen atoms.

19. The compound according to claim 1, wherein R and R$^1$ are independently selected from the group of
radicals of formula (II)

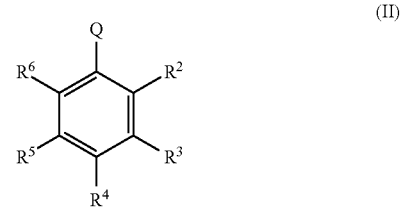 (II)

wherein, R$^2$, R$^3$, R$^4$, R$^5$, and R$^6$ are independently selected from the group of
hydrogen,
linear or branched C$_1$-C$_8$-alkyl,
—NH—C(=O)—R$^{14}$, —C(=O)—NH—R$^{14}$,
wherein R$^{14}$ is linear or branched C$_1$-C$_8$-alkyl,
—C(=O)OR$^{15}$, wherein R$^{15}$ is linear or branched C$_1$-C$_8$-alkyl, and
halogen, or
R$^2$ and R$^3$, or R$^4$ and R$^5$ or both, or
R$^3$ and R$^4$, or R$^5$ and R$^6$ or both, or
R$^2$ and R$^3$ as well as R$^5$ and R$^6$ together form a hydrocarbon diradical comprising 3 or 4 carbon atoms;

and

Q is a single bond or branched or unbranched $C_1$-$C_8$-alkylene, optionally comprising one or more oxygen atoms.

* * * * *